(12) United States Patent
Hirai et al.

(10) Patent No.: US 9,569,836 B2
(45) Date of Patent: Feb. 14, 2017

(54) DEFECT OBSERVATION METHOD AND DEFECT OBSERVATION DEVICE

(71) Applicant: Hitachi High-Technologies Corporation, Minato-ku, Tokyo (JP)

(72) Inventors: Takehiro Hirai, Tokyo (JP); Ryo Nakagaki, Tokyo (JP); Minoru Harada, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/650,515

(22) PCT Filed: Nov. 29, 2013

(86) PCT No.: PCT/JP2013/082117
§ 371 (c)(1),
(2) Date: Jun. 8, 2015

(87) PCT Pub. No.: WO2014/103611
PCT Pub. Date: Jul. 3, 2014

(65) Prior Publication Data
US 2015/0302568 A1 Oct. 22, 2015

(30) Foreign Application Priority Data

Dec. 28, 2012 (JP) .................................. 2012-286608

(51) Int. Cl.
*G06K 9/00* (2006.01)
*G06T 7/00* (2006.01)
(Continued)

(52) U.S. Cl.
CPC ............ *G06T 7/001* (2013.01); *G01N 23/2254* (2013.01); *G06K 9/00* (2013.01); *G06K 9/46* (2013.01);
(Continued)

(58) Field of Classification Search
CPC ........... G06T 2207/30148; G06T 7/001; G06T 7/0004; G06T 7/004; G06T 2207/20148; G06T 2207/10016; G06T 7/0006; G06T 7/0002; G01N 21/9501; G01N 21/956; G01N 2223/611; G01N 2021/8825; G01N 21/95607; G01N 21/8903; G01N 2223/418; G01N 2021/95676; G01N 21/9505; G01N 23/2254; G06K 2209/19; G06K 9/00; G06K 2209/19; G06K 9/46; H01J 37/244; H01J 2237/2817; H01J 37/222; H01J 37/21; G01R 31/311; G01R 31/318511; G11B 27/34; H01L 27/14659; H01L 22/12; H04N 5/32; H04N 9/8042; H04N 9/3182; B82Y 40/00; B23K 26/066; G03F 1/84
(Continued)

(56) References Cited

U.S. PATENT DOCUMENTS 6,947,587 B1 * 9/2005 Maeda .............. G01N 21/95607
382/144
2001/0028733 A1 * 10/2001 Sasaki .................. G01N 21/956
382/149
(Continued)

FOREIGN PATENT DOCUMENTS

JP 2007-40910 A 2/2007
JP 2009-250645 A 10/2009
(Continued)

OTHER PUBLICATIONS

International Search Report (PCT/ISA/210) dated Mar. 4, 2014, with English translation (Four (4) pages).

*Primary Examiner* — Vu Le
*Assistant Examiner* — Aklilu Woldemariam
(74) *Attorney, Agent, or Firm* — Crowell & Moring LLP

(57) ABSTRACT

Cases in which defects are analyzed in a manufacturing process stage in which a pattern is not formed or in a manufacturing process in which a pattern formed on a lower layer does not appear in the captured image are increasing. However, in these cases, there is a problem of not being able to synthesize a favorable reference image and failing to detect a defect when a periodic pattern cannot be recognized in the pattern. In the present invention, a defect occupation rate, which is the percentage of an image being inspected occupied by a defect region, is found, it is determined whether the defect occupation rate is higher or lower than a threshold, and, in accordance with the determination results, it is determined whether to create, as the reference image, an (Continued)

image comprising pixels having the average luminance value of the luminance values of a plurality of pixels contained in the image being inspected. In particular, when the defect occupation rate is low, an image comprising pixels having the average luminance value of the luminance values of a plurality of pixels contained in the image being inspected is used as the reference image.

13 Claims, 19 Drawing Sheets

(51) Int. Cl.
*G01N 23/225* (2006.01)
*G06K 9/46* (2006.01)
(52) U.S. Cl.
CPC ....... *G06K 9/4661* (2013.01); *G01N 2223/418* (2013.01); *G01N 2223/611* (2013.01); *G06K 2009/4666* (2013.01); *G06T 2207/30148* (2013.01)
(58) Field of Classification Search
USPC ... 382/141, 144, 145, 149, 151, 170; 348/80
See application file for complete search history.

(56) References Cited

U.S. PATENT DOCUMENTS

| | | | | |
|---|---|---|---|---|
| 2005/0147287 A1* | 7/2005 | Sakai | ................. | G01N 21/9501 382/141 |
| 2005/0275833 A1* | 12/2005 | Silver | ................. | G06K 9/4609 356/237.1 |
| 2006/0159330 A1* | 7/2006 | Sakai | ..................... | G06T 7/001 382/141 |
| 2006/0159333 A1* | 7/2006 | Ishikawa | ................. | G06T 7/001 382/149 |
| 2006/0215901 A1* | 9/2006 | Nakagaki | ................ | G06T 7/001 382/149 |
| 2006/0257015 A1* | 11/2006 | Katahata | ................ | G06T 7/001 382/145 |
| 2007/0031026 A1 | 2/2007 | Kurihara et al. | | |
| 2007/0071307 A1* | 3/2007 | Isomura | .................. | G06T 7/001 382/149 |
| 2008/0130982 A1* | 6/2008 | Kitamura | ................. | G06K 9/00 382/144 |
| 2008/0226156 A1* | 9/2008 | Ota | .................... | G01R 31/2836 382/141 |
| 2008/0247630 A1* | 10/2008 | Horiuchi | ............ | G01N 21/9501 382/141 |
| 2008/0317329 A1* | 12/2008 | Shibuya | ................ | G06T 7/0004 382/149 |
| 2009/0252403 A1 | 10/2009 | Harada et al. | | |
| 2009/0268959 A1 | 10/2009 | Harada et al. | | |
| 2010/0128119 A1* | 5/2010 | Takahashi | ................ | G06T 7/001 348/126 |
| 2011/0285839 A1 | 11/2011 | Kotaki et al. | | |
| 2011/0299760 A1 | 12/2011 | Harada et al. | | |
| 2012/0156810 A1* | 6/2012 | Fukazawa | .......... | G01N 21/9501 438/16 |
| 2013/0128026 A1* | 5/2013 | Hirose | ............... | G01N 21/8903 348/125 |

FOREIGN PATENT DOCUMENTS

| | | |
|---|---|---|
| JP | 2009-283917 A | 12/2009 |
| JP | 2010-161247 A | 7/2010 |
| JP | 2010-197221 A | 9/2010 |

\* cited by examiner

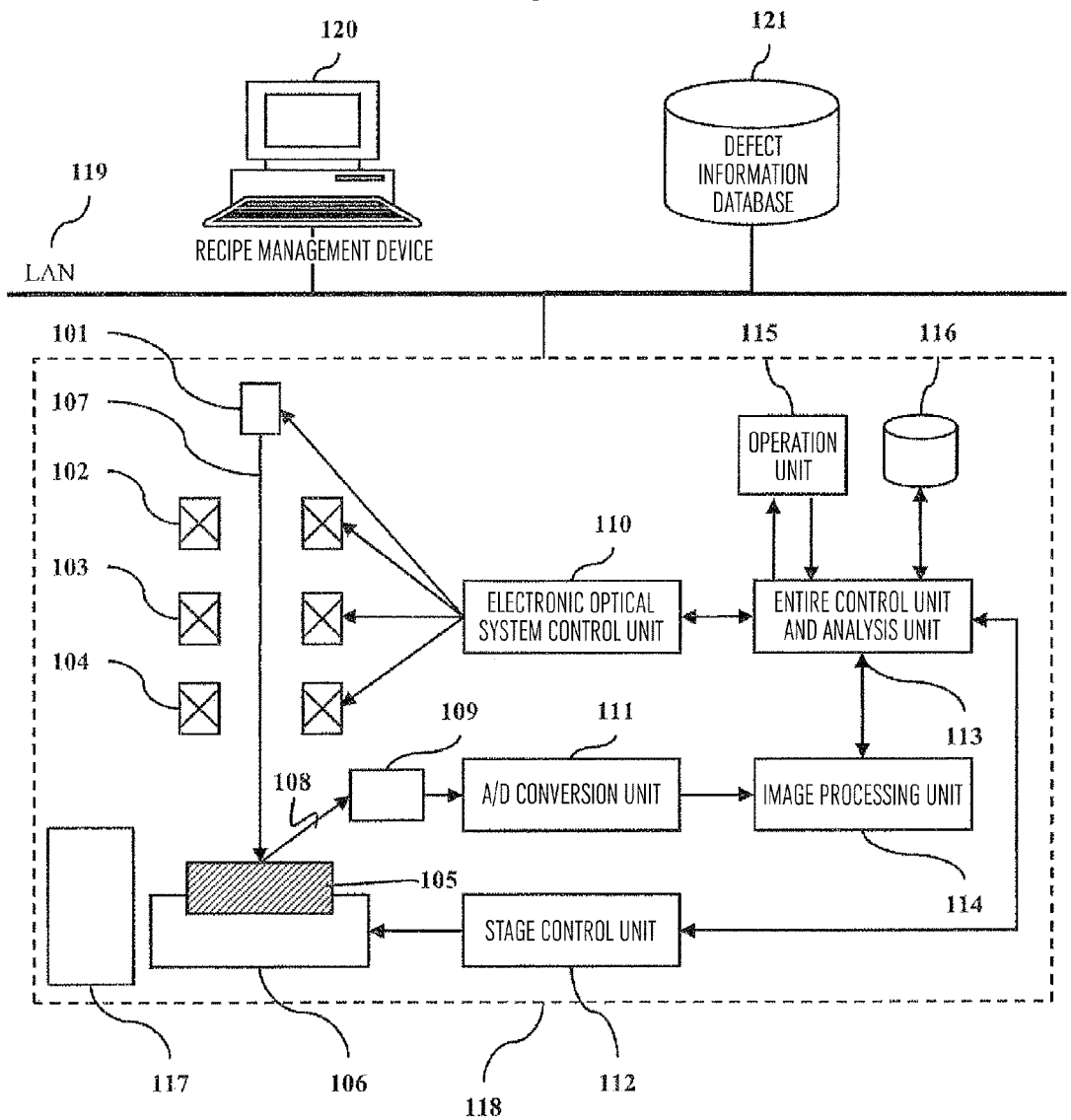
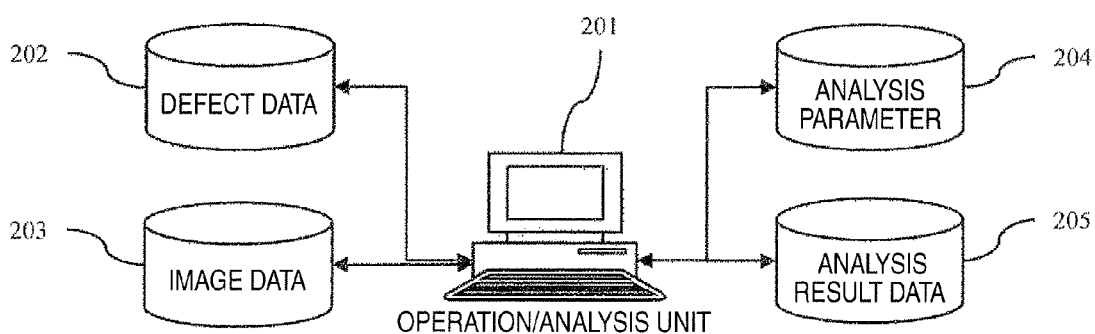

DEFECT OBSERVATION METHOD AND DEFECT OBSERVATION DEVICE

TECHNICAL FIELD

The present invention relates to a defect observation method and a defect observation device in a semiconductor manufacturing process.

BACKGROUND ART

In a semiconductor manufacturing process, it is important to discover a defect occurring in the manufacturing process early and take measures, to secure a high yield.

A scanning electron microscope (SEM)-type defect observation device (also called a defect review device) is a device to observe a defect occurred in the semiconductor manufacturing process, particularly. The SEM-type defect observation device is generally a device to observe an image of the defect coordinates detected by an upper defect inspection device with definition higher than definition in the upper defect inspection device. Specifically, the SEM-type defect observation device moves a sample stage to the defect coordinates output by the upper defect inspection device, executes imaging with a low magnification where a defect to be observed enters a view, detects the defect coordinates from an imaged low-magnification image, moves the sample stage such that the defect is positioned at the center of the view or moves the center of the imaging, and acquires a high-magnification image for observation with the high magnification suitable for the defect observation.

As such, the defect coordinates are detected from the low-magnification image, because error is included in the defect coordinates output by the upper defect inspection device, in a range of a device specification, and processing for correcting the error is necessary when the high-definition defect image is acquired by the SEM-type defect observation device.

Automatic defect review or automatic defect redetection (ADR) automates a process for acquiring the high-definition defect image. In the ADR, an acquisition condition of the low-magnification image to detect the defect or an acquisition condition of the high-magnification image to observe the defect should be optimized while a balance of the defect detection rate and the throughput of the ADR is considered, according to coordinate precision of defect detection in the upper defect inspection device, a characteristic of a sample, or a kind of the defect to be observed.

Patent Literature 1 describes "acquiring an image including a defect with a first magnification using a scanning electron microscope, generating a reference image from the acquired image including the defect with the first magnification, comparing the acquired image including the defect with the first magnification and the reference image generated from the image including the defect with the first magnification to detect the defect, and imaging the detected defect with a second magnification larger than the first magnification. According to this, "because a process for imaging the reference image with the low magnification can be omitted, the defect can be reviewed more efficiently" is described.

CITATION LIST

Patent Literature

Patent Literature 1: JP-A-2007-40910 (US 2007/0031026 A)

SUMMARY OF INVENTION

Technical Problem

Recently, with miniaturization of a design pattern and complexity of a manufacturing process, defects affecting the yield diversify and manufacturing processes to be observation targets increase. Particularly, a case in which a minute detect not brought into question in the past also becomes an observation target and in a manufacturing process of a step in which a pattern is not formed or a manufacturing process in which a pattern formed on a lower layer does not appear in an imaging image, erroneous detection of a false defect is accepted to some extent, a supersensitive defect inspection is executed, defect candidates detected including the false defect are observed by a defect observation device, and a real defect is analyzed increases.

However, for a combination of a reference image in the above case, when a periodic pattern cannot be recognized in a defect image, a superior reference image cannot be combined and defect detection is not successfully executed, in the method that combines a reference image not including the defect, using periodicity of the pattern manufactured from the defect image including the defect, as in Patent Literature 1.

For this reason, there is a need to develop a method of generating a reference image to be suitable for the case in which a pattern does not exist in a view of an image and a defect observation system capable of stably realizing high-precision defect detection using the generated reference image.

Solution to Problem

In order to resolve the above problems, the present invention is characterized in that a defect occupation rate to be a ratio of a defect area in an inspected image is calculated, the magnitude of the defect occupation rate and a threshold value is determined, and it is determined whether an image configured by pixels having an average brightness value of a plurality of pixels included in the inspected image is generated as the reference image, according to a result of the determination.

Advantageous Effects of Invention

According to the present invention, a method of generating a reference image to be suitable for the case in which a pattern does not exist in a view of an image and a defect observation system capable of stably realizing high-precision defect detection using the generated reference image can be provided.

Other objects, configurations, and effects of the present invention will become apparent from the following description of embodiments of the present invention.

BRIEF DESCRIPTION OF DRAWINGS

FIG. 1 is an example of a schematic configuration diagram of an SEM-type defect observation system.

FIG. 2 is an example of a configuration diagram of an operation/analysis unit of the SEM-type defect observation system.

DESCRIPTION OF EMBODIMENTS

Figure 3:
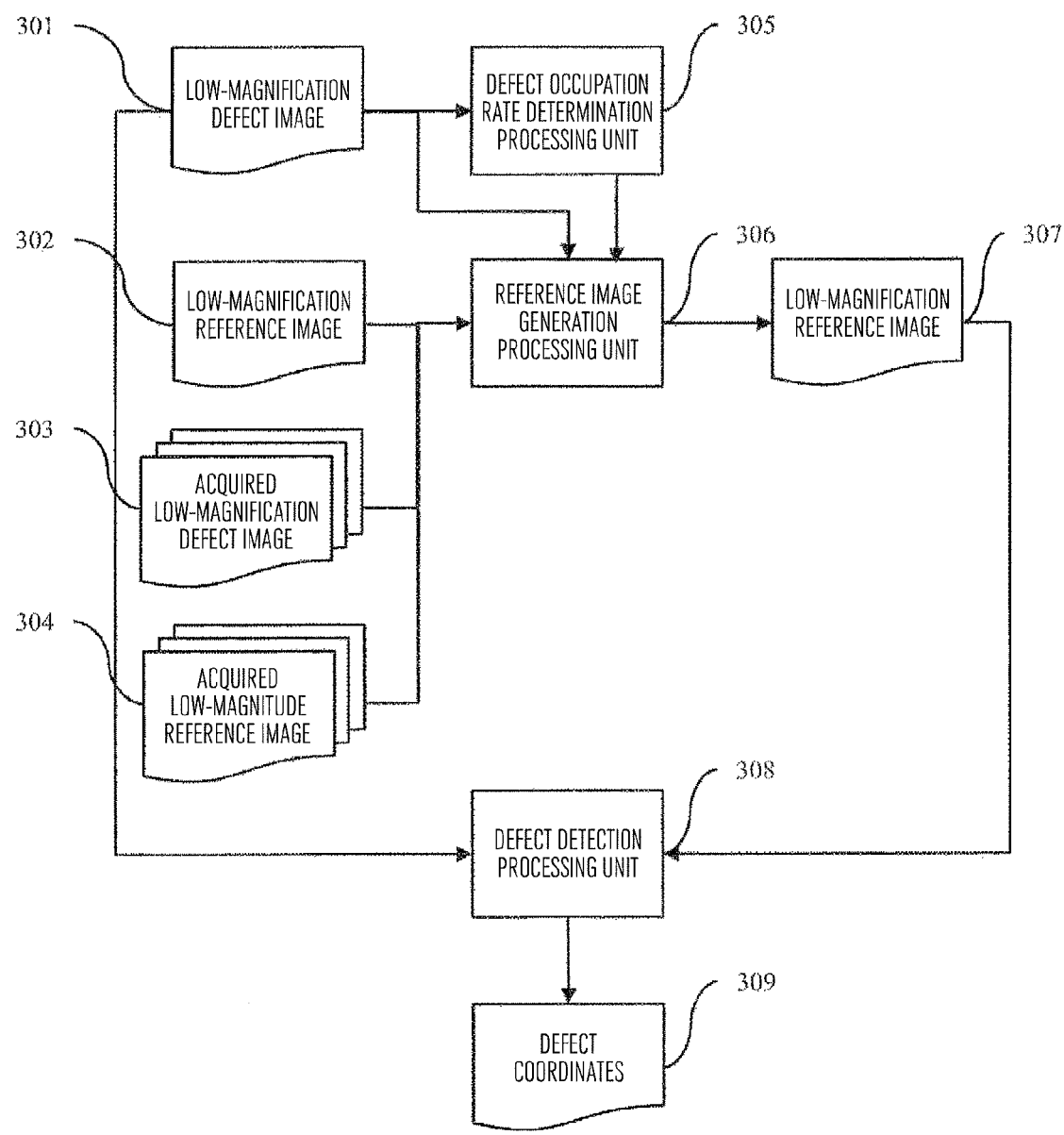
FIG. 3 is an example of a functional block diagram in the operation/analysis unit to execute defect detection.

Configuration examples of a defect detection method, a defect observation device, and a defect observation system to be stable in which both the defect detection precision and the throughput are realized even when a pattern does not exist in a view of an image will be described. The defect observation system to be described below is an example of the present invention and the present invention is not limited to embodiments to be described below. In the present invention, the defect observation device is a device to image an image of a sample using a charged particle beam and includes devices to detect a defect by comparing a plurality of images widely. In addition, the defect observation system is a system in which the defect observation device is connected to other device by a network and includes systems including the defect observation device widely.

As one configuration example of the defect observation system including the defect observation device, an example of the case in which a defect image is acquired by ADR in an SEM-type defect observation device is described. However, a system configuration is not limited thereto and a part or all of devices configuring the defect observation system may be configured by different devices. For example, ADR processing according to this embodiment may be executed by an ADR processing device or an image management device connected to the SEM-type defect observation device by the network or a review management device and may be executed by a program executing desired operation processing by a central processing unit (CPU) mounted in a general-purpose computer in the system. In addition, an existing device can be upgraded by a storage medium on which the program is recorded.

In the present specification, the "defect" is not limited to a foreign material and includes observation target materials such as a material defect or a structure defect of a sample widely.

In addition, in the present specification, the "sample" may be a process of a step after a pattern is manufactured as well as a wafer of a process of a step before the pattern is manufactured. The embodiments to be described below are effective particularly when the pattern is not imaged or does not exist in a view of an observation image, regardless of whether the pattern is actually manufactured.

In addition, in the present specification, a "defect image" is an image for which a defect is inspected (inspected image) and includes defect candidate images or false defect images as well as a real defect image. A "reference image" is a so-called standard image used for comparison with the defect image to extract the defect and is an image of a normal area, that is, an area estimated as an area not having a defect.

Hereinafter, the embodiments of the present invention will be described in detail with reference to the drawings.

Embodiment 1

The SEM-type defect observation device is a device that acquires a high-definition SEM image of the defect coordinates under a condition suitable for observation or analysis, using the defect coordinates detected by a defect inspection device such as an optical-type or SEM-type inspection device as input information. As the information input to the SEM-type observation device, in addition to the defect coordinates detected by the defect inspection device, coordinate information of an observation point extracted by simulation based on design layout data can be used.

FIG. 1 is a schematic diagram illustrating an entire configuration of an SEM-type observation system in this embodiment. An SEM-type defect observation device 118 of FIG. 1 includes an electronic optical system configured by optical elements such as an electron gun 101, a lens 102, a scanning deflector 103, an objective lens 104, a sample 105, and a secondary particle detector 109, a stage 106 to move a sample stand holding a sample to be observed in an XY plane, an electronic optical system control unit 110 to control the various optical elements included in the electronic optical system, an A/D conversion unit 111 to quantize an output signal of the secondary particle detector 109, a stage control unit 112 to control the stage 106, an entire control/analysis unit 113, an image processing unit 114, an operation unit 115 including a display, a keyboard, and a mouse, a storage device 116 to store an acquired image, and an optical microscope 117. The electronic optical system, the electronic optical system control unit 110, the A/D conversion unit 111, the stage 106, and the stage control unit 112 configure a scanning electronic microscope to be an imaging unit of an SEM image.

A primary electron beam 107 emitted from the electron gun 101 is converged by the lens 102, is deflected by the scanning deflector 102, is converged by the objective lens 104, and is emitted to the sample 105. From the sample 105 to which the primary electron beam 107 has been emitted, a secondary particle 108 such as a secondary electron or a reflection electron is generated according to a shape or a material of the sample. The generated secondary particle 108 is detected by the secondary particle detector 109 and is converted into a digital signal by the A/D conversion unit 111. An output signal of the secondary particle detector converted into the digital signal is also called an image signal. The output signal of the A/D conversion unit 111 is output to the image processing unit 114 and forms an SEM image. Of course, in addition to the components, other lens, electrode, and detector may be included in the device, partial components may be different from the components, and a configuration of a charged particle optical system is not limited thereto.

The image processing unit 114 executes various image analysis processing such as ADR processing to execute image processing such as defect detection and automatic defect classification (ADC) processing to automatically classify defects for each kind, using the generated SEM image. In the SEM-type observation device according to this embodiment, images of an observation target can be acquired with a plurality of different magnifications. For example, the observation target can be observed by changing a scanning range of the scanning deflector 103 and changing the magnification.

Control of the optical elements in the electronic optical system such as the lens 102, the scanning deflector 103, and the objective lens 104 is executed by the electronic optical system control unit 110. Positional control of the sample is executed by the stage 106 controlled by the stage control unit 112. The entire control/analysis unit 113 is a control unit that wholly controls the entire SEM-type observation device and interprets input information from the operation unit 115 including the display, the keyboard, and the mouse and the storage device 116, controls the electronic optical system control unit 110, the stage control unit 112, and the image processing unit 114, and outputs a processing result to a display unit included in the operation unit 115 or the storage device 116 according to necessity.

The processing executed by the image processing unit 114 may be configured as hardware by a dedicated circuit board and may be realized by software executed by a computer connected to the defect observation device. When the processing is configured by the hardware, the processing can be realized by integrating a plurality of operation units executing the processing into a wiring substrate, a semiconductor chip, or a package. When the processing is configured by the software, the processing can be realized by mounting a high-speed CPU to the image processing unit 114 and executing a desired operation process by a program.

FIG. 1 illustrates an example of the case in which the SEM-type defect observation device 118, a recipe management device 120, and a defect information database 121 are connected by a local area network (LAN) 119 as an example the defect observation system. An image acquired by the SEM-type defect observation device 118 is stored in the defect information database 121. In addition, information regarding the defect, for example, an imaging condition of the defect image or the detected defect coordinates is stored in the defect information database 121. The recipe management device 120 acquires defect information necessary for recipe preparation from the defect information database 121, executes operation processing including image processing, and prepares a recipe in which a condition and a sequence to execute the ADR or ADC processing are recorded. A parameter used for the operation processing or the prepared recipe may be stored in a storage device embedded in the recipe management device and may be stored in the defect information database. As such, the "defect information" includes information regarding the defect, such as the coordinates of the defect detected by the inspection device, an image imaged by the inspection device, a result analyzed by an analysis function of the inspection device, the coordinates of the defect detected again by the defect observation device, an image imaged by the defect observation device, and a result analyzed by an analysis function of the defect observation device.

FIG. 2 is an example of a detailed diagram of the entire control unit and analysis unit 113, the operation unit 115, and the storage device 116 of FIG. 1. Here, an operation/analysis unit 201 is obtained by integrating the entire control/analysis unit 113 and the operation unit 115 of FIG. 1. The operation/analysis unit 201 includes a plurality of functional blocks realized by executing a predetermined program by a CPU embedded in the entire control/analysis unit 113, according to an operation instruction from the operation unit 115. As such, a configuration is not limited to a configuration in which the entire control/analysis unit illustrated in FIG. 1 is embedded in the SEM-type observation device and the operation/analysis unit 201 illustrated in FIG. 2 may be configured independently form the SEM-type observation device illustrated in FIG. 1 and the components of FIGS. 1 and 2 may be coupled by network connection.

When the components of FIG. 2 are embedded in the defect observation system of FIG. 1, a defect data storage unit 202, an image data storage unit 203, an analysis parameter storage unit 204, and an analysis result data storage unit 205 may be integrated into the storage device 116 of FIG. 1.

Defect information such as the defect coordinates is stored in the defect data storage unit 201. A defect image imaged by the SEM-type observation device is stored in the image data storage unit 202. Conditions such as an ADR condition and an ADC condition executed when an image is acquired or analyzed are stored in the analysis parameter storage unit 204 and the analysis parameter storage unit 204 can reproduce the plurality of conditions. A processing result is stored in the analysis result data storage unit 205.

As another embodiment, a function of the operation/analysis unit 201 can be realized by the recipe management device 120 in the SEM-type defect observation system illustrated in FIG. 1. In addition, the defect data storage unit 202, the image data storage unit 203, the analysis parameter storage unit 204, and the analysis result data storage unit 205 can be realized by the defect information database 121 in the SEM-type defect observation system illustrated in FIG. 1.

FIG. 3 is an example of a block diagram of a function to execute defect detection processing to be described below. In the functional block diagram of FIG. 3, all of functions corresponding to all of the following embodiments are illustrated to simplify the description, but only a part thereof may be mounted to the device. The details will be described in the individual embodiments.

A reference image generation processing unit 306 generates a low-magnification reference image from a low-magnification defect image, using methods described in the following embodiments. As described after Embodiment 2, when the low-magnification reference image is not combined and a newly imaged low-magnification reference image is used, an acquired low-magnification reference image 302 is output as an image for a comparison target as it is. A defect detection processing unit 308 uses a low-magnification defect image 301 and a low-magnification reference image 307 as input information to detect a difference area of these images as a defect area. Detected defect coordinates 309 are output as defect coordinate information to acquire a high-magnification image.

A defect occupation rate determination processing unit 305 determines a defect occupation rate using the low-magnification defect image 301 imaged by the SEM-type observation device as input information. The details will be described after Embodiment 2. In this case, the reference image generation processing unit 306 determines a reference image generation method, on the basis of a result determined by the defect occupation rate determination processing unit 305. The low-magnification reference image 307 is generated using the low-magnification defect image 301, the low-magnification reference image 302, an acquired low-magnification defect image 303, or an acquired low-magnification reference image 304 as input information, on the basis of the determined generation method. Here, "acquired" means that a defect image other than the defect image 301 corresponding to an inspected target is imaged in the past. A method using the acquired low-magnification defect image or the acquired low-magnification reference image will be described in detail in Embodiments 3 to 5.

As such, a method of generating a low-magnification reference image used for defect detection is optimized on the basis of a defect occupation rate of a low-magnification defect image to be an analysis target, so that precision of the defect detection can be improved. In addition, because an operator does not need to select the acquisition or generation method of the low-magnification reference image by automating processing for optimizing the method of generating the low-magnification reference image, on the basis of the defect occupation rate, the workload can be reduced.

Figure 4:
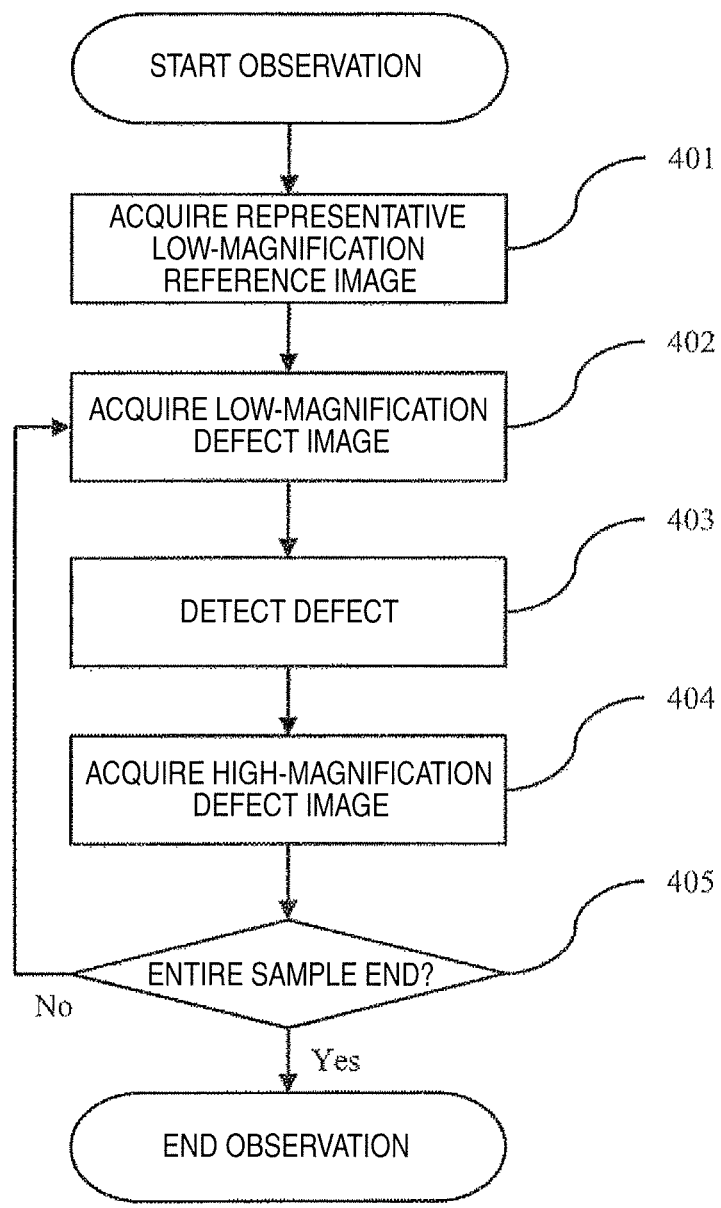
FIG. 4 is an example of an ADR flowchart to acquire a representative reference image.

FIG. 4 is an example of a flowchart of ADR to acquire a representative low-magnification reference image in the first of an ADR sequence. A low-magnification reference image corresponding to a low-magnification defect image does not need to be acquired every time for a sample when a pattern does not exist in a view of an image, that is, in a manufacturing process of a step in which the pattern is not formed or a state in which a pattern formed in a lower layer does not appear in an imaging image by application of a film material. Therefore, for high-speed processing, one low-magnification reference image is acquired in the first of the ADR sequence and the acquired low-magnification reference image and each low-magnification defect image are compared and defect detection is performed. As such, an acquired representative image is called the "representative low-magnification reference image" to be used as a comparison standard of each low-magnification defect image.

First, the representative low-magnification reference image is acquired in the first of the ADR sequence (401). Because it is important not to include the pattern to be manufactured in the defect or the sample in the representative low-magnification reference image, an image of the center coordinates of the sample in which the possibility of the pattern not existing is high or the coordinates designated by the recipe by the user is acquired. When the defect is included in the representative low-magnification reference image, a difference other than the defect to be observed is detected at the time of detecting a difference with the low-magnification defect image. For this reason, the defect detection is not successfully executed.

Next, the sample stage is moved such that the coordinates of the observation target enter a view and the low-magnification defect image is acquired (402). The acquired low-magnification defect image and the representative low-magnification reference image acquired in the first of the sequence are compared and a difference is detected as a defect area (403). At the coordinates of the detected defect area, a high-magnification defect image is acquired with a magnification suitable for observation (404). Here, the magnification suitable for the observation is generally a magnification higher than the magnification of the low-magnification image. Processing of 402 to 404 is executed on the entire samples and the entire inspection target points of the observation target (405). As such, the low-magnification reference image is not acquired for each observation target and the representative low-magnification reference image is acquired in the first of the ADR sequence and is repetitively used. As a result, the throughput can be improved.

Figure 5:
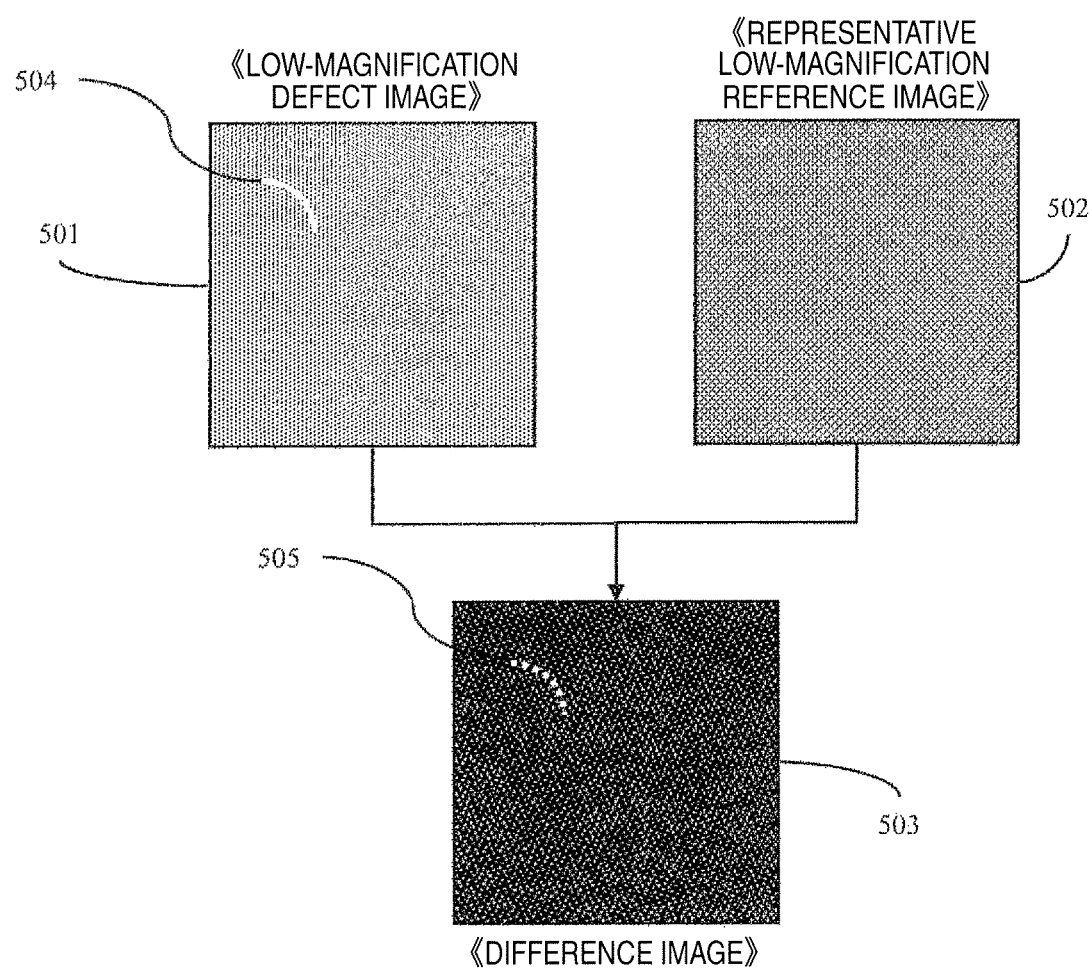
FIG. 5 is an example of a schematic diagram illustrating a defect detection method using a representative reference image.

FIG. 5 is an example of a schematic diagram illustrating defect detection processing using the representative low-magnification reference image. A problem of the method described in FIG. 4 will be described using the schematic diagram. In a method using the representative low-magnification reference image, a defect image 501 and a representative low-magnification reference image 502 are compared and a difference image 503 is acquired. The difference image 503 is acquired by comparing the low-magnification defect image 501 and the representative low-magnification reference image 502 in a unit of a pixel and it is determined that a significant difference exists when a difference of gradation values is equal to or more than a threshold value in the difference image 503. In the difference image 503, pixels in which it is determined that the significant difference exists are shown by white and pixels in which it is determined that the significant difference does not exist are shown by black. Hereinafter, in the present specification, a white portion is described as an area determined as a defect portion and a black portion is described as an area determined as a normal portion.

In the case of FIG. 5, a defect 504 having a curved line shape exists on the low-magnification defect image 501 and a defect area 505 is detected on the difference image 503. However, the defect area 505 is detected in a broken line shape by an influence of noises existing in the representative low-magnification reference image 502. In addition to the defect area 505, a difference, which may be a cause of erroneous detection of the defect, is extracted from the difference image 503 by an influence of noises existing in the low-magnification defect image 501 and the representative low-magnification reference image 502.

Technology for reducing noises at the time of imaging or technology for reducing an influence of noises by image processing is developed. However, this processing is insufficient and defect detection processing that is suitable for when a pattern does not exist in a view of an image and has a low operation cost and robustness against a noise is demanded. Particularly, in the SEM-type observation device, because a charged state is changed by a material of a sample or a difference of a structure and visibility of an acquired image is changed, defect detection processing corresponding to the change in the visibility of the representative low-magnification reference image and the low-magnification defect image is demanded.

According to the technology disclosed in Patent Literature 1, the reference image becoming the comparison target is combined with the defect image. For this reason, if the technology is compared with the method described in FIG. 5, an advantage of the technology is that a difference of the visibility of the defect image and the reference image, for example, a variation of a brightness distribution decreases. However, there is a problem in the defection detection precision and the throughput.

First, for the defect detection precision, there is a problem in that precision of reference image combination using periodicity is bad, when a pattern does not exist in a view of an image. If a defect area remains in the combined reference image, the possibility of the defect being missed or an area other than the defect being erroneously detected becomes high, as compared with the defect image.

Next, for the throughput, there is a problem in that it is necessary to calculate the periodicity of the defect image, divide an image according to the periodicity, and recombine the divided images and an operation cost is high to combine the reference image and the throughput is deteriorated. The processing for combining the reference image using the pattern in the view of the observation is repetitively executed for each defect image, that is, by the number of observation targets. For this reason, when a total of processing time is longer than acquisition time of the representative reference image described in FIG. 4, a method of acquiring the representative low-magnification reference image once in the first of the ADR sequence is at an advantage in terms of the throughput.

Figure 6:
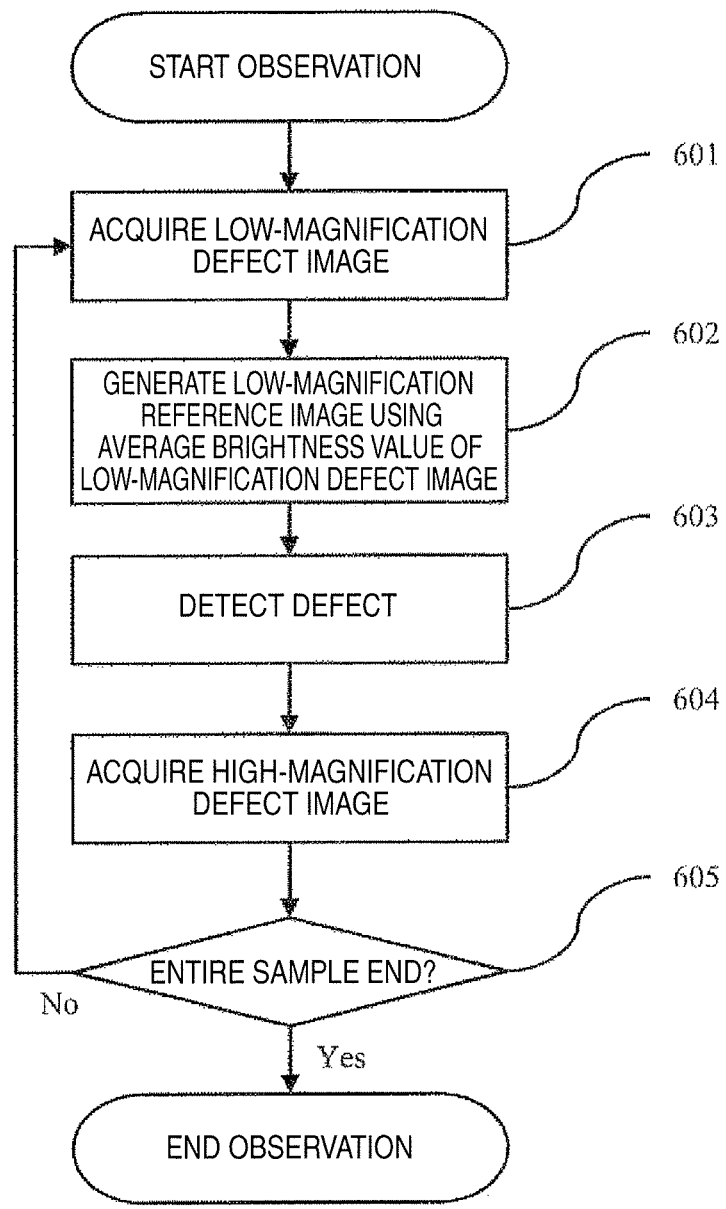
FIG. 6 is an example of an ADR flowchart according to Embodiment 1.

Therefore, a processing method to resolve a problem when the technology described in FIG. 4 or 5 or the technology disclosed in Patent Literature 1 is applied to the case in which the pattern does not exist in the view of the image will be described. FIG. 6 is an example of a flowchart of the ADR according to this embodiment.

First, the low-magnification defect image is acquired (601). As compared with FIG. 4, because it is not necessary to acquire the representative low-magnification reference image in the first of the sequence, processing time for acquisition processing of the representative low-magnification reference image can be decreased.

Next, a low-magnification reference image is generated using an average brightness value of the acquired low-magnification defect image (602). The processing for generating the low-magnification reference image needs to be executed for each low-magnification defect image. However, as compared with Patent Literature 1, because an average value is only calculated simply and the processing is simple, the low-magnification reference image can be generated in short time. In addition, processing for calculating an average brightness value can be generally executed at a speed higher than a speed when noise reduction processing is executed on the low-magnification defect image, the low-magnification reference image, and the difference image. Here, the "average brightness value" is an average brightness value of entire pixels configuring the low-magnification defect image or a representative brightness value. For example, when the low-magnification defect image is configured by 500×500 pixels, an image of 500×500 pixels is configured such that an average of entire pixel values of a total of 250,000 pixels is used as an average brightness value and all of the pixels have the average brightness value. In the SEM image, because the brightness values are represented often by 256 gradations from 0 to 255 in gray scale, the average brightness value takes a value between 0 and 255 in that case.

Finally, the low-magnification reference image generated by 602 and the low-magnification defect image acquired by 601 are compared, a difference is detected as a defect area, and the defect coordinates are detected (603). At the detected defect coordinates, a high-magnification defect image is acquired with a magnification suitable for the observation, generally, a magnification higher than a magnification of the low-magnification defect image (604). Processing of 601 to 604 is executed on entire samples and entire inspection target points of the observation target (605).

Figure 7:
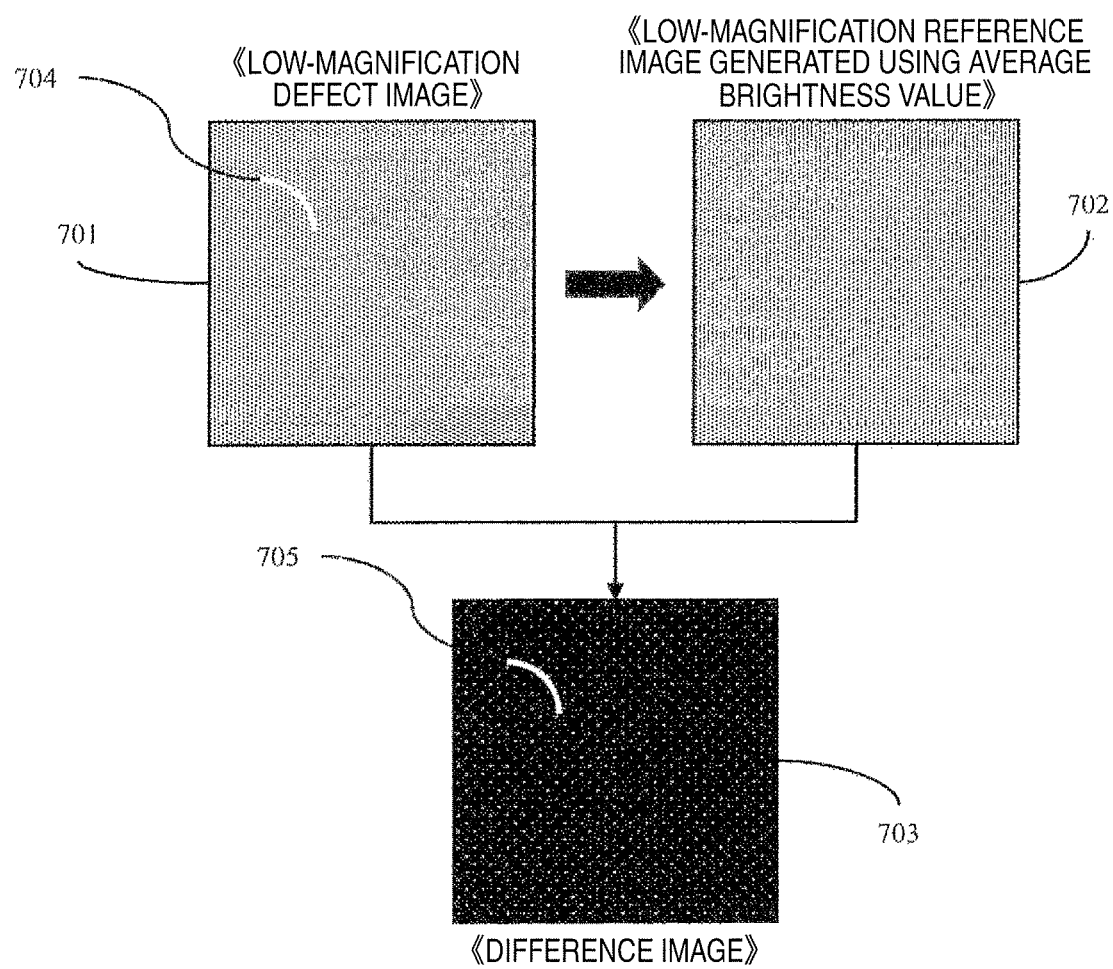
FIG. 7 is an example of a schematic diagram illustrating the defect detection method according to Embodiment 1.

FIG. 7 is an example of a schematic diagram illustrating defect detection processing using the low-magnification reference image generated using the average brightness value of the low-magnification defect image described in FIG. 6. A low-magnification defect image 701 and a low-magnification reference image 702 generated using an average brightness value of the low-magnification defect image are compared and it is determined that a significant difference exists when a difference of the gradation values is equal to or more than a threshold value. In a difference image 703, pixels in which it is determined that the significant difference exists are shown by white and pixels in which it is determined that the significant difference does not exist are shown by black.

Similar to the case of FIG. 5, in the case of FIG. 7, a defect 704 having a curved line shape exists on the low-magnification defect image 701 and a defect area 705 is detected on the difference image 703. As compared with the defect area 505 of FIG. 5, because noises do not exist in the low-magnification reference image 702, the defect area is extracted more correctly. In addition to the defect area 705 to be detected, a part of the noises existing on the defect image 701 remains on the difference image 703. However, as compared with the difference image 503 of FIG. 5, because the noises do not exist in the low-magnification reference image 702, the difference area other than the defect decreases.

As such, the low-magnification defect image 301 is used as an input, the low-magnification reference image 307 is generated using the average brightness value of the low-magnification defect image 301 by the reference image generation processing unit 306, the low-magnification defect image 301 and the low-magnification reference image 307 are compared by the defect detection processing unit 308, and a difference can be output as the defect coordinates 309. According to this method, because the low-magnification reference image generated using the average brightness value of the low-magnification defect image is used, stable defect detection can be realized for the change in the noises or the visibility of the representative low-magnification reference image, as compared with the method using the representative low-magnification reference image. In addition, because the low-magnification reference image can be generated by a simple operation like calculation of the average brightness value of the low-magnification defect image, high-speed defect detection processing can be realized.

Embodiment 2

In this embodiment, an example of a defect detection method in which great importance is attached to stability of defect detection rather than a processing speed as compared with the method described in Embodiment 1 will be described. Because the configurations described in FIGS. 1 to 3 and the content described in FIGS. 4 to 7 are the same as those in this embodiment, explanation thereof is omitted.

Figure 8:
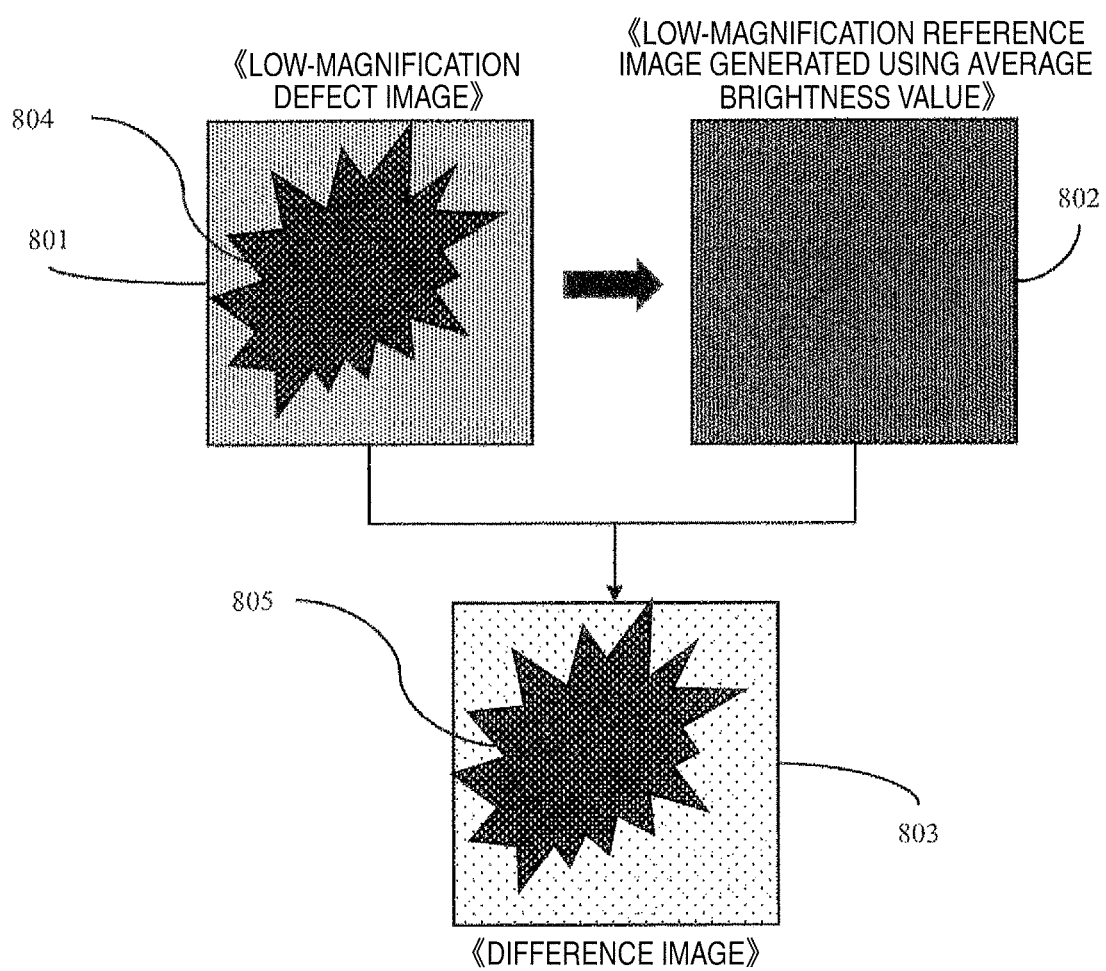
FIG. 8 is an example of a schematic diagram illustrating a problem of the defect detection method according to Embodiment 1.

FIG. 8 is a schematic diagram illustrating a problem of the defect detection method using the low-magnification reference image generated using the average brightness value of the low-magnification defect image, described in FIGS. 6 and 7. The problem when the low-magnification reference image is generated using the average brightness value of the low-magnification defect image is that, when a size of a defect area occupied in the low-magnification defect image is relatively large, a calculated average brightness value is affected by a brightness value of the defect area. A "defect occupation rate" is a ratio of a defect area occupied in an entire view of an image. Because the defect area is normally small in the view of the image, the defect occupation rate is relatively small. However, when a defect to be detected is a so-called enormous defect, the defect occupation rate increases.

As illustrated in FIG. 8, when a defect 804 in which a defect occupation rate for the view of the observation is high exists in a low-magnification defect image 801, a low-magnification reference image 802 generated using an average brightness value of the low-magnification defect image 801 is affected by a pixel value of a portion of the defect 804 having the high occupation rate. It is ideal that the low-magnification reference image is generated using an average brightness of an area other than the defect area. However, in the case of FIG. 8, because the brightness of the defect area 804 in the low-magnification defect image 801 is low (dark) and the brightness of the area other than the defect area is high (bright), the brightness of the generated low-magnification reference image 802 is low (dark) as compared with the ideal low-magnification reference image. For this reason, in a difference image 803 obtained by comparing the low-magnification defect image 801 and the low-magnification reference image 802 and calculating a difference as the defect area, a defect area 805 for detection is determined as a non-defect area (in the drawing, a black portion). Meanwhile, a background portion to be determined as the non-defect area is erroneously detected as a defect area (in the drawing, a white portion).

As such, the method of generating the low-magnification reference image using the average brightness value of the low-magnification defect image described in Embodiment 1 has a problem in that defect detection precision decreases, when a defect occupation rate is large in the low-magnification defect image.

Figure 9:
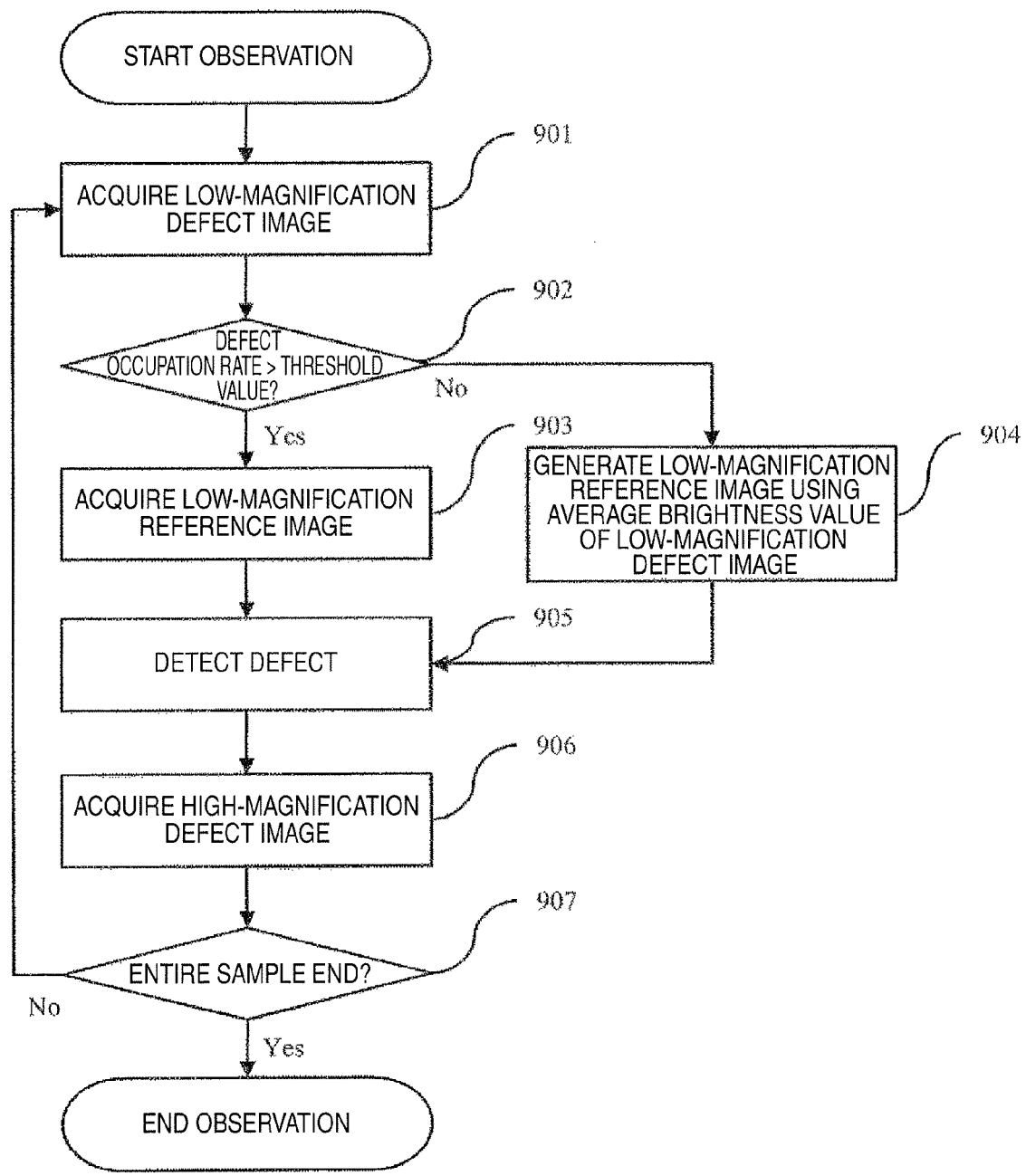
FIG. 9 is an example of an ADR flowchart according to Embodiment 2.

A method to resolve a problem in that defect detection precision decreases when a defect occupation rate in the low-magnification defect image described in FIG. 8 is high will be described using FIG. 9. FIG. 9 is an example of a flowchart of ADR to change a low-magnification reference image according to a defect occupation rate of a defect image. That is, FIG. 9 is an example of the case in which, when the defect occupation rate is high, the reference image is acquired and when the defect occupation rate is low, the low-magnification reference image is generated by the method according to Embodiment 1.

First, a low-magnification defect image is acquired (901). Next, an occupation rate (defect occupation rate) of a defect area in the acquired low-magnification defect image is calculated and the magnitude with a predetermined threshold value is determined (902). On the basis of a determination result, it is determined whether a low-magnification reference image is generated using an average brightness value of the low-magnification defect image. Specifically, when a defect occupation rate is low, it is determined that a method of generating the low-magnification reference image using the average brightness value of the low-magnification defect image is effective and the low-magnification reference image is generated from the average brightness value of the low-magnification defect image, using the same method as the method described in FIG. 6 or 7 (904). Meanwhile, in the case in which the defect occupation rate is high, if the low-magnification reference image is generated from the average brightness value of the low-magnification defect image, the possibility of the low-magnification reference image not being generated using the desired brightness value due to an influence of the defect area having the high defect occupation rate is high. For this reason, an image of the coordinates where it can be expected that the defect does not exist is acquired newly as the low-magnification reference image (903). Here, the magnitude of the defect occupation rate may be determined by a certain threshold value, as in the method illustrated in Embodiment 8.

Next, the low-magnification reference image acquired by 903 or the low-magnification reference image generated by 904 and the low-magnification defect image acquired by 901 are compared and a difference thereof is detected as a defect area (905). From the detected defect area, a high-magnification defect image is acquired with a magnification higher than a magnification suitable for the observation, generally, a magnification higher than a magnification of the low-magnification defect image (906). Works of 901 to 906 are executed on the entire samples and inspection target points (907).

Figure 10:
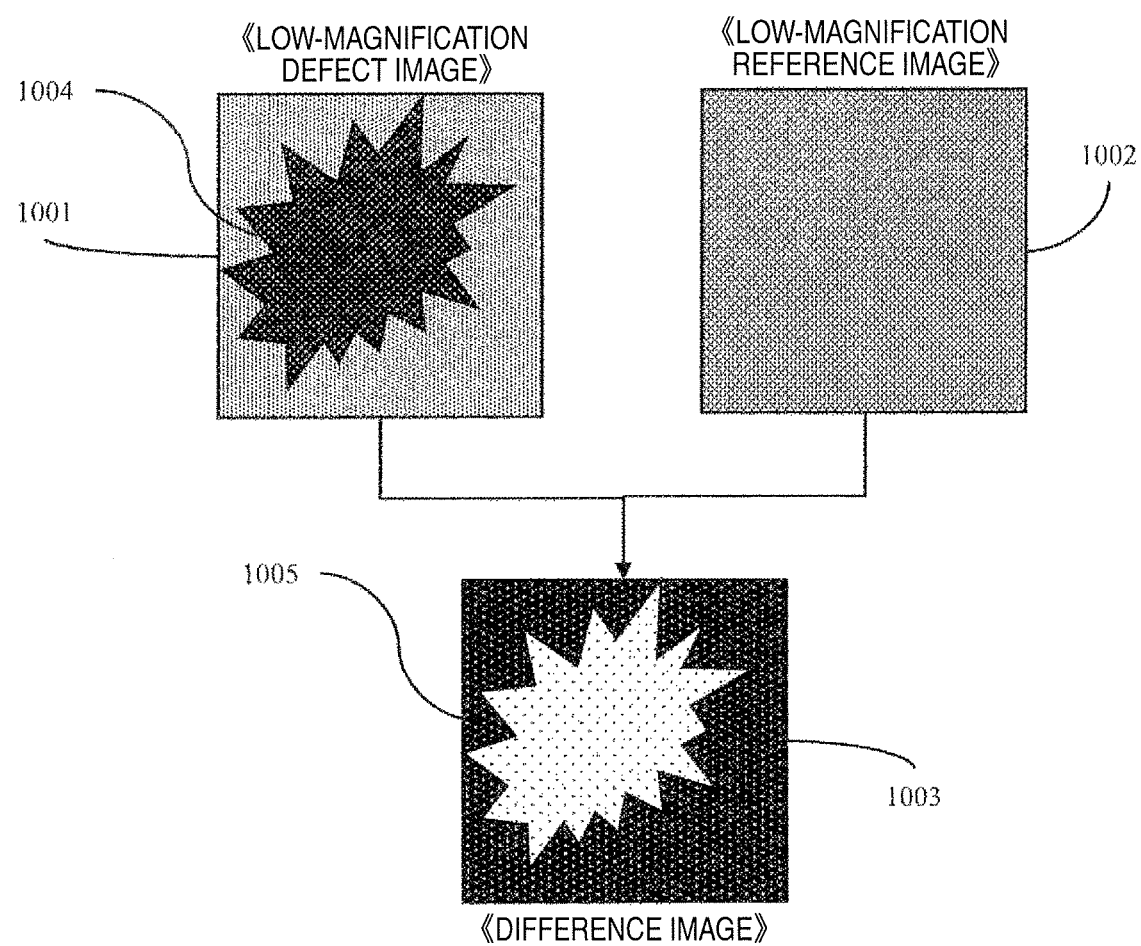
FIG. 10 is an example of a schematic diagram illustrating a defect detection method according to Embodiment 2.

FIG. 10 is an example of a schematic diagram illustrating the defect detection method described in FIG. 9. When it is determined that a defect area 1004 is large and a defect occupation rate is high, in a low-magnification defect image 1001, an image of the coordinates where it can be expected that the defect does not exist is acquired without generating the low-magnification reference image from the low-magnification defect image and the image is used as a low-magnification reference image 1002. Meanwhile, when it is determined that the defect area is small and the defect occupation rate is low, using the same method as the method described in FIG. 6 or 7, the image generated from the average brightness value of the low-magnification defect image is used as the low-magnification reference image.

Next, the low-magnification defect image 1001 and the low-magnification reference image 1002 are compared and a difference image 1003 is acquired. When the low-magnification defect image 1001 and the low-magnification reference image 1002 are compared in a unit of a pixel and a difference of gradation values is equal to or more than a threshold value, it is determined that a significant difference exists. In the difference image 1003 of FIG. 10, a portion in which it is determined that the significant difference exists is shown by white and a portion in which it is determined that the significant difference does not exist is shown by black.

As such, the defect occupation rate is calculated by the defect occupation rate determination processing unit 305 using the low-magnification defect image 301 as an input. When the defect occupation rate is high, the reference image generation processing unit 306 newly images the low-magnification reference image 302 and when the defect occupation rate is low, the reference image generation processing unit 306 generates the low-magnification reference image 307 from the average brightness value of the low-magnification defect image. The defect detection processing unit 308 compares the low-magnification defect image 301 and the low-magnification reference image 307 output from the reference image generation processing unit 306 and outputs a difference as the defect coordinates 309.

According to this method, when the defect occupation rate of the low-magnification defect image is low, the low-magnification reference image generated using the average brightness value of the low-magnification defect image is used for the defect detection, so that stable defect detection can be realized for the change in the brightness due to the noises or the material quality or structure at the observation coordinates. When the defect occupation rate of the low-magnification defect image is high, an image of the coordinates where it is can be expected that the defect does not exist is acquired and used as the low-magnification reference image. Therefore, a defect detection rate can be prevented from decreasing. From the viewpoint of the processing speed, if the number of times of acquiring the low-magnification reference image increases, the throughput of the ADR decreases. However, the observation condition of the low-magnification defect image is set without excessively increasing the magnification of the low-magnification defect image (excessively narrowing the view of the observation), so that the defect image in which the defect occupation rate is high can be suppressed from being generated.

Embodiment 3

In this embodiment, an embodiment of a defect observation method in which a decrease in processing speed is minimally suppressed while great importance is attached to stability of defect detection as compared with the method described in Embodiment 1 will be described. As compared with Embodiment 2, the stability of the defect detection is the same and the processing speed is high. Because the configurations described in FIGS. 1 to 3 and the content described in FIGS. 4 to 7 are the same as those in this embodiment, explanation thereof is omitted.

Similar to the method of acquiring the representative reference image described in FIG. 5, the method described in Embodiment 2 has a problem in that an influence of noises of a low-magnification reference image is easily received and defect detection precision is deteriorated. Control is enabled by magnification adjustment at the time of acquiring the low-magnification defect image. However, as described in FIG. 9, if the case in which it is determined that a defect occupation rate is high increases, processing for acquiring the low-magnification reference image is necessary. For this reason, the throughput decreases.

Figure 11:
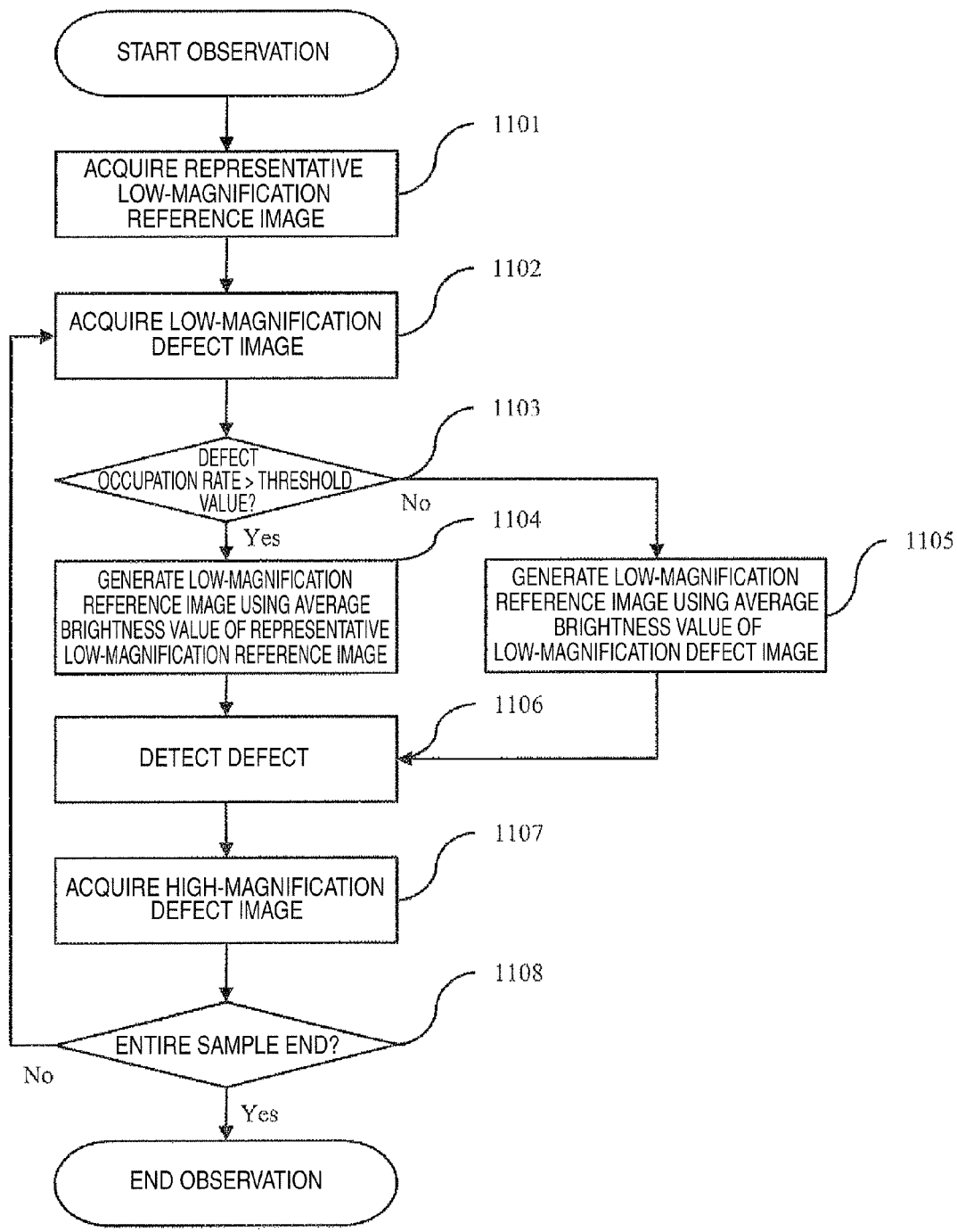
FIG. 11 is an example of an ADR flowchart according to Embodiment 3.

FIG. 11 is an example of a flowchart of ADR to generate a low-magnification reference image using an average brightness value of a representative low-magnification reference image, when the defect occupation rate of the low-magnification defect image is high. A method to resolve the problem in the method in which the image of the coordinates where it can be expected that the defect does not exist is acquired and is used as the low-magnification reference image, when the defect occupation rate of the low-magnification defect image is high, described in Embodiment 2, will be described.

First, an image of the coordinates in which it can be expected that the defect does not exist is acquired in the first of an ADR sequence and the image is set as a representative low-magnification reference image (1101). Next, a low-magnification defect image is acquired (1102) and a defect occupation rate of a defect area in the acquired low-magnification defect image is calculated and the magnitude with a predetermined threshold value is determined (1103). On the basis of a determination result, it is determined whether a low-magnification reference image is generated using an average brightness value of the low-magnification defect image. Specifically, when a defect occupation rate is low, it is determined that a method of generating the low-magnification reference image using the average brightness value of the low-magnification defect image is effective and the low-magnification reference image is generated from the average brightness value of the low-magnification defect image (1105). Meanwhile, when the defect occupation rate is high, the low-magnification reference image is generated using the average brightness value of the representative low-magnification reference image acquired by 1101 (1104).

Finally, the low-magnification reference image generated using the average brightness value of the representative low-magnification reference image or the low-magnification reference image generated using the average brightness value of the low-magnification defect image and the low-magnification defect image acquired by 1102 are compared and a difference is detected as a defect area (1106). Next, an enlarged high-magnification defect image of the detected defect area is acquired (1107) and processing of 1102 to 1107 is executed on entire samples and inspection target points (1108).

Figure 12:
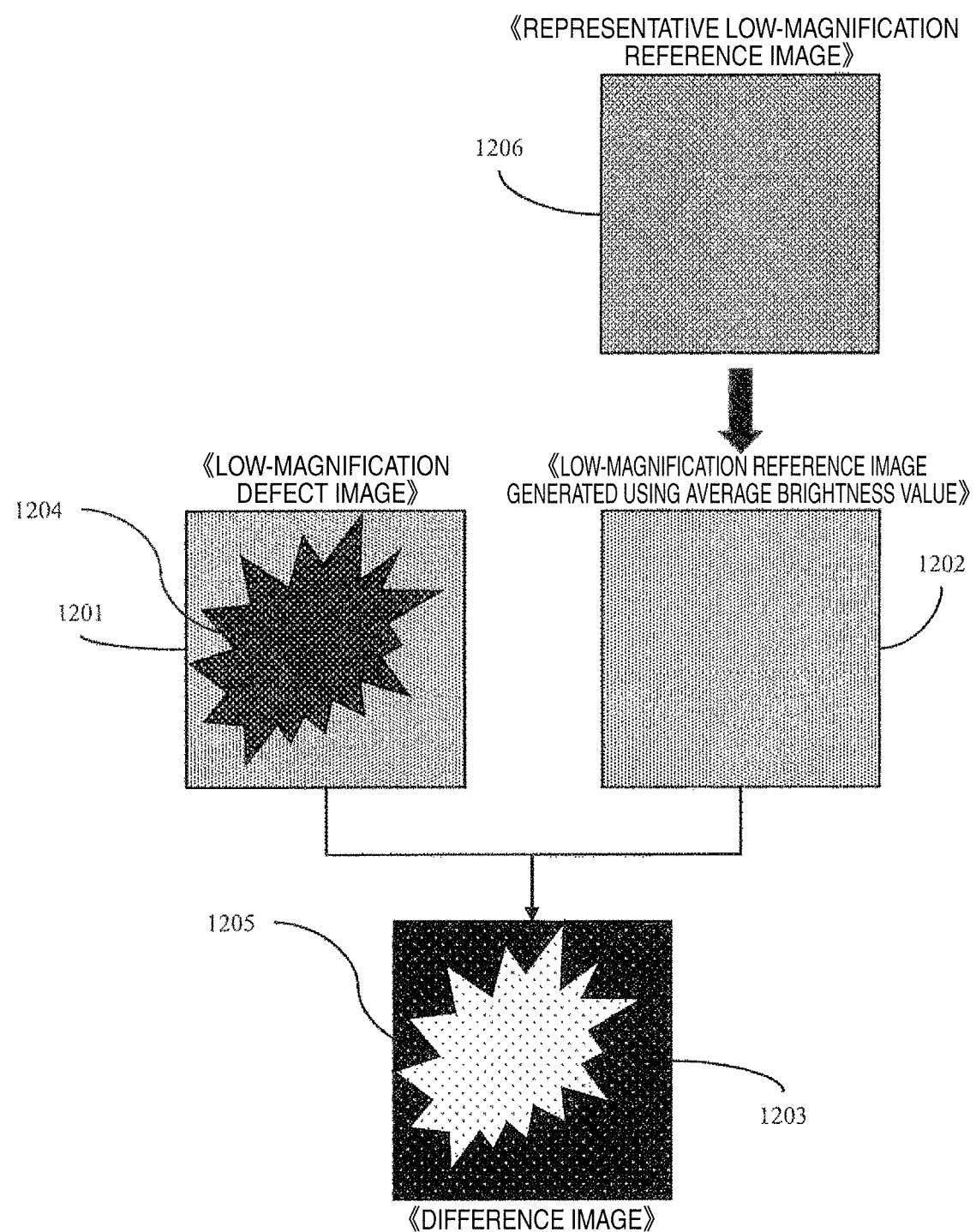
FIG. 12 is an example of a schematic diagram illustrating a defect detection method according to Embodiment 3.

FIG. 12 is an example of a schematic diagram illustrating the defect detection method described in FIG. 11. First, a low-magnification reference image 1202 is generated from the average brightness value of the representative low-magnification reference image 1206 acquired in the first of the ADR sequence. The defect occupation rate of the acquired low-magnification defect image 1201 is calculated. When the defect occupation rate is high, the low-magnification defect image 1201 and the low-magnification reference image 1202 are compared and a difference image 1203 is acquired. Meanwhile, when it is determined that the defect area is small and the defect occupation rate is low, using the same method as the method described in FIG. 6 or 7, the image generated from the average brightness value of the low-magnification defect image is used as the low-magnification reference image.

In the difference image 1203 of FIG. 12, it is determined that a significant difference exists, when the low-magnification defect image 1201 and the low-magnification reference image 1202 are compared in a unit of a pixel and a difference of gradation values is equal to or more than a threshold value. In the difference image 1203, pixels in which it is determined that the significant difference exists are shown by white and images in which it is determined that the significant difference does not exist are shown by black.

As such, the defect occupation rate is calculated by the defect occupation rate determination processing unit 305 using the low-magnification defect image 301 as an input. When the defect occupation rate is high, the reference image generation processing unit 306 generates the low-magnification reference image 307 from the average brightness value of the representative low-magnification reference image and when the defect occupation rate is low, the reference image generation processing unit 306 generates the low-magnification reference image 307 from the average brightness value of the low-magnification reference image. The defect detection processing unit 308 compares the low-magnification defect image 301 and the low-magnification reference image 307 output from the reference image generation processing unit 306 and outputs a difference as the defect coordinates 309.

According to this method, when the defect occupation rate is low, the low-magnification reference image generated using the average brightness value of the low-magnification defect image is used for the defect detection, so that stable defect detection can be realized for the change in the brightness due to the noises or the material quality or structure at the observation coordinates. When the defect occupation rate of the low-magnification defect image is high, the low-magnification reference image is generated using the average brightness value of the representative low-magnification reference image. Therefore, the defect detection is enabled without being affected by the defect area of the low-magnification defect image and the defect detection rate can be prevented from decreasing. In addition, the low-magnification reference image is generated from the average brightness of the representative low-magnification reference image, so that it is difficult to receive an influence of the noises of the representative low-magnification reference image, as compared with the case in which the representative low-magnification reference image is used as it is, and high-precision defect detection is enabled. In addition, the representative reference image is acquired once in the first of the sequence, so that a decrease in the throughput by the low-magnification reference image acquisition can be minimally suppressed, as compared with the method of acquiring the low-magnification reference image whenever the defect occupation rate is high.

Embodiment 4

In this embodiment, an example of a defect observation method for realizing stable defect detection by using a reference image acquired or generated in the past will be described. Because the configurations described in FIGS. 1 to 3 and the content described in FIGS. 4 to 7 are the same as those in this embodiment, explanation thereof is omitted.

A defect detection method suitable for an observation target can be selected by the methods described in Embodiments 1 to 3, in consideration of a balance of the defect detection precision and the throughput. However, when one recipe is repetitively used for different processes, the possibility of visibility of a background portion being different due to a difference of a material quality or a structure of a sample is high. For this reason, a stable correspondence method is demanded for this case.

In addition, in a method of acquiring one representative reference image in the first of a sequence, like the ADR sequence described in Embodiment 3, it is not guaranteed that the representative reference image is an ideal reference image. The ideal reference image is an image in which a manufacturing pattern or a structure of a lower layer does not appear in a view and brightness irregularities by noises or charging of a sample do not occur at the same brightness as a brightness of the background portion of the defect image. It is rare, but there is the case in which the representative reference image is not the ideal reference image. For this reason, a stable method is demanded for this case.

Figure 13:
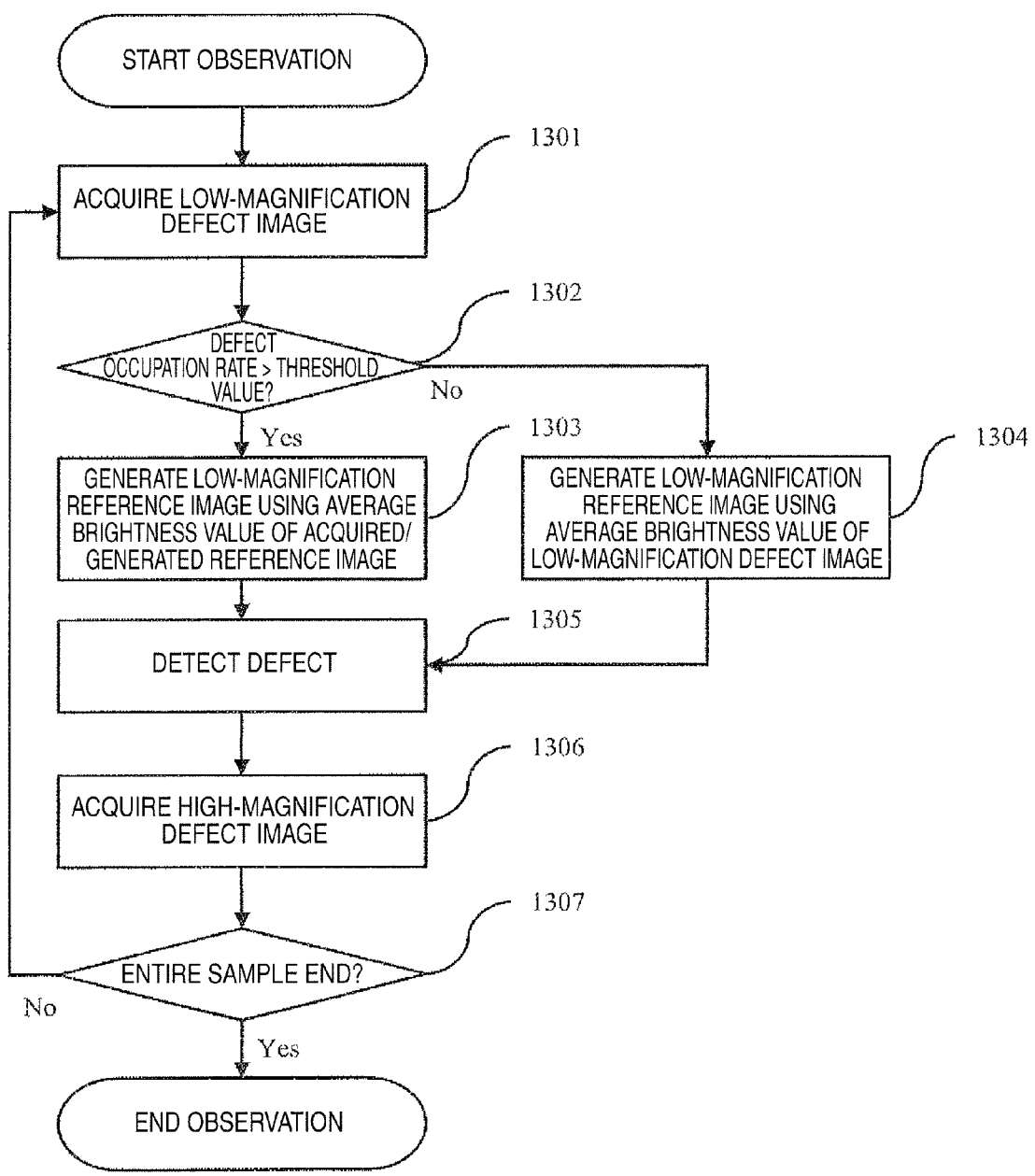
FIG. 13 is an example of an ADR flowchart according to Embodiment 4.

FIG. 13 is a flowchart of ADR to generate a low-magnification reference image using an average brightness value of an acquired or generated reference image, when the defect occupation rate of the low-magnification defect image is high. First, a low-magnification defect image is acquired (1301) and an occupation rate of a defect area in the acquired low-magnification defect image is calculated and the magnitude with a predetermined threshold value is determined (1302). On the basis of a determination result, it is determined whether a low-magnification reference image is generated using an average brightness value of the low-magnification defect image. Specifically, when a defect occupation rate is low, it is determined that a method of generating the reference image using the average brightness value of the low-magnification defect image is effective and the low-magnification reference image is generated from the average brightness value of the low-magnification defect image (1304). Meanwhile, when the defect occupation rate is high, the low-magnification reference image is generated using an average brightness value of the acquired reference image or the generated reference image (1303). Here, the acquired reference image or the generated reference image is not limited to a low-magnification reference image acquired or generated in the ADR sequence at the time of the observation and may include a reference image acquired or generated in the past, in a recipe considered as having the same image quality. The reference image may be automatically selected and may be designated by a recipe by selection of an operator. A plurality of acquired or generated low-magnification reference images are selected and a low-magnification reference image can be generated using an average brightness value of the entire images.

In FIG. 13, because the low-magnification reference image is generated using the average brightness value of the acquired or generated reference image (1303) after defect occupation rate determination processing (1302), a newest low-magnification reference image generated in the ADR sequence can be used. Thereby, stable defect detection according to a change in visibility by a material quality or a structure at an observation point can be expected.

However, if a low-magnification reference image is generated every time, an operation cost increases. For this reason, the low-magnification reference image may be generated in advance at an average brightness of an acquired or generated reference image, before the ADR sequence starts. The generated low-magnification reference image may be registered in a recipe in which an execution condition of the ADR is described, for example. In this way, the low-magnification reference image having considered the reference image acquired or generated in the past can be used without deteriorating the throughput of the ADR. Therefore, stable defect detection can be realized.

Next, the low-magnification reference image generated by 1303 or the low-magnification reference image generated by 1304 and the low-magnification defect image acquired by 1301 are compared and a difference is detected as a defect area (1305). Finally, an enlarged image of the detected defect area is acquired as a high-magnification defect image (1306). Processing of 1301 to 1306 is executed on entire samples and inspection target points (1307).

Figure 14:
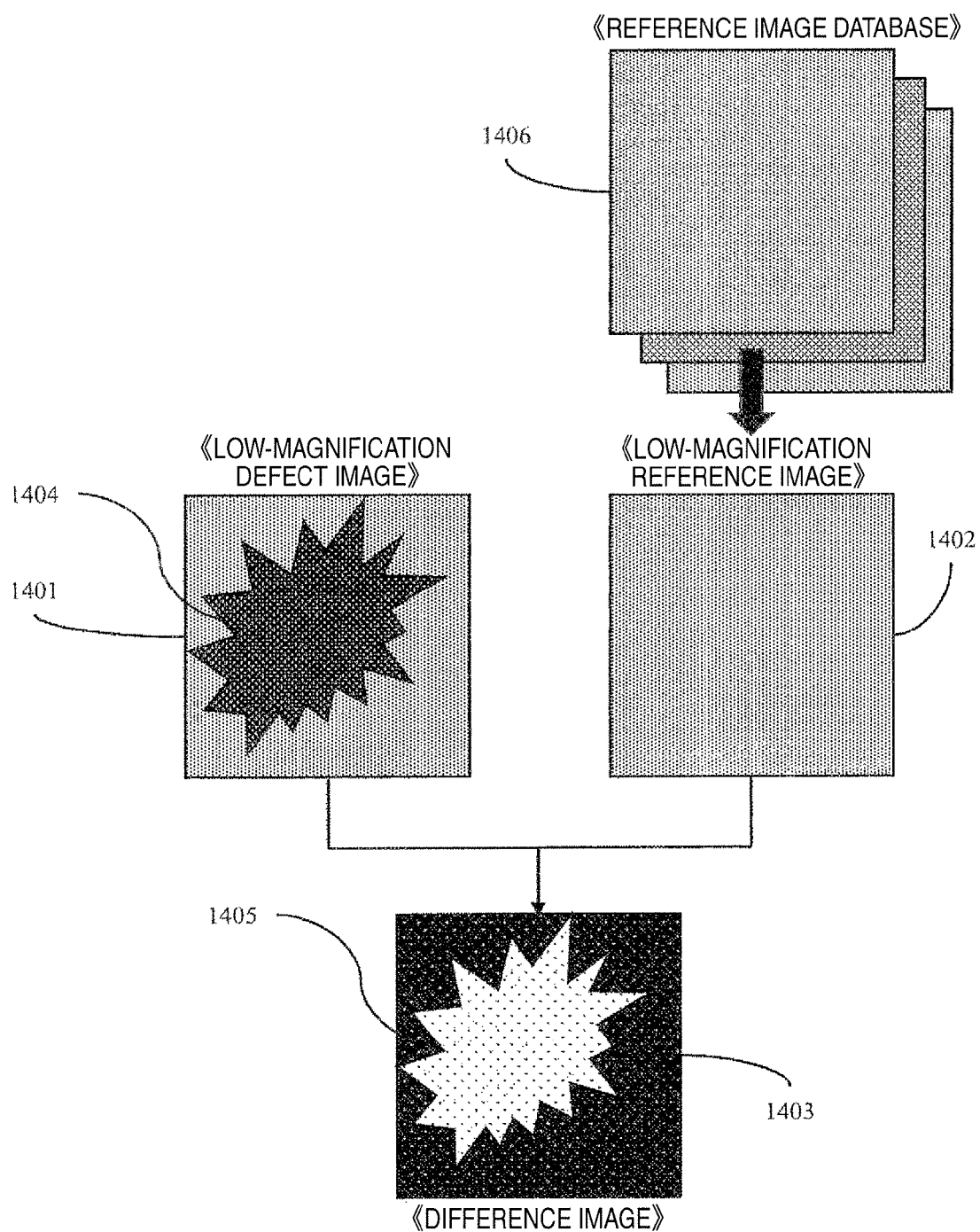
FIG. 14 is an example of a schematic diagram illustrating a defect detection method according to Embodiment 4.

FIG. 14 is an example of a schematic diagram illustrating the defect detection method described in FIG. 13.

First, a low-magnification reference image 1402 is generated using an average brightness value of one or more acquired or generated reference images 1406. A defect occupation rate of the acquired low-magnification defect image 1401 is calculated. When the defect occupation rate is high, the low-magnification defect image 1401 and the low-magnification reference image 1402 are compared in a unit of a pixel. Meanwhile, when it is determined that the defect area is small and the defect occupation rate is low, using the same method as the method described in FIG. 6 or 7, the image generated from the average brightness value of the low-magnification defect image is used as the low-magnification reference image and the low-magnification reference image and the low-magnification defect image are compared. When a difference of gradation values is equal to or more than a threshold value by comparison, it is determined that a significant difference exists. In the difference image 1403, pixels in which it is determined that the significant difference exists are shown by white and pixels in which it is determined that the significant difference does not exist are shown by black.

As such, the defect occupation rate is calculated by the defect occupation rate determination processing unit 305 using the low-magnification defect image 301 as an input. When the defect occupation rate is high, the reference image generation processing unit 306 generates the low-magnification reference image 307 using the average brightness value of the acquired low-magnification reference image 304 and when the defect occupation rate is low, the reference image generation processing unit 306 generates the low-magnification reference image 307 from the average brightness value of the low-magnification defect image. The defect detection processing unit 308 compares the low-magnification defect image 301 and the low-magnification reference image 307 output from the reference image generation processing unit 306 and outputs a difference as the defect coordinates 309.

According to this method, when the defect occupation rate is low, the low-magnification reference image generated using the average brightness value of the low-magnification defect image is used for the defect detection, so that stable defect detection can be realized for the change in the brightness due to the noises or the material quality or structure at the observation coordinates. When the defect occupation rate of the low-magnification defect image is high, the average brightness value is calculated from one or more acquired reference images and the low-magnification reference image is generated using the average brightness value. Therefore, stable generation of the low-magnification reference image is enabled for the change in the brightness due to the noises or the material quality or structure at the observation coordinates. The case in which the representative reference image is not the ideal reference image, which rarely occurs, can be avoided.

Embodiment 5

In this embodiment, an example of a defect observation method that generates a reference image using an average brightness value of an area other than a defect area from a defect image acquired in the past and realizes stable defect detection using the reference image will be described. Because the configurations described in FIGS. 1 to 3 and the content described in FIGS. 4 to 7 are the same as those in this embodiment, explanation thereof is omitted.

Figure 15:
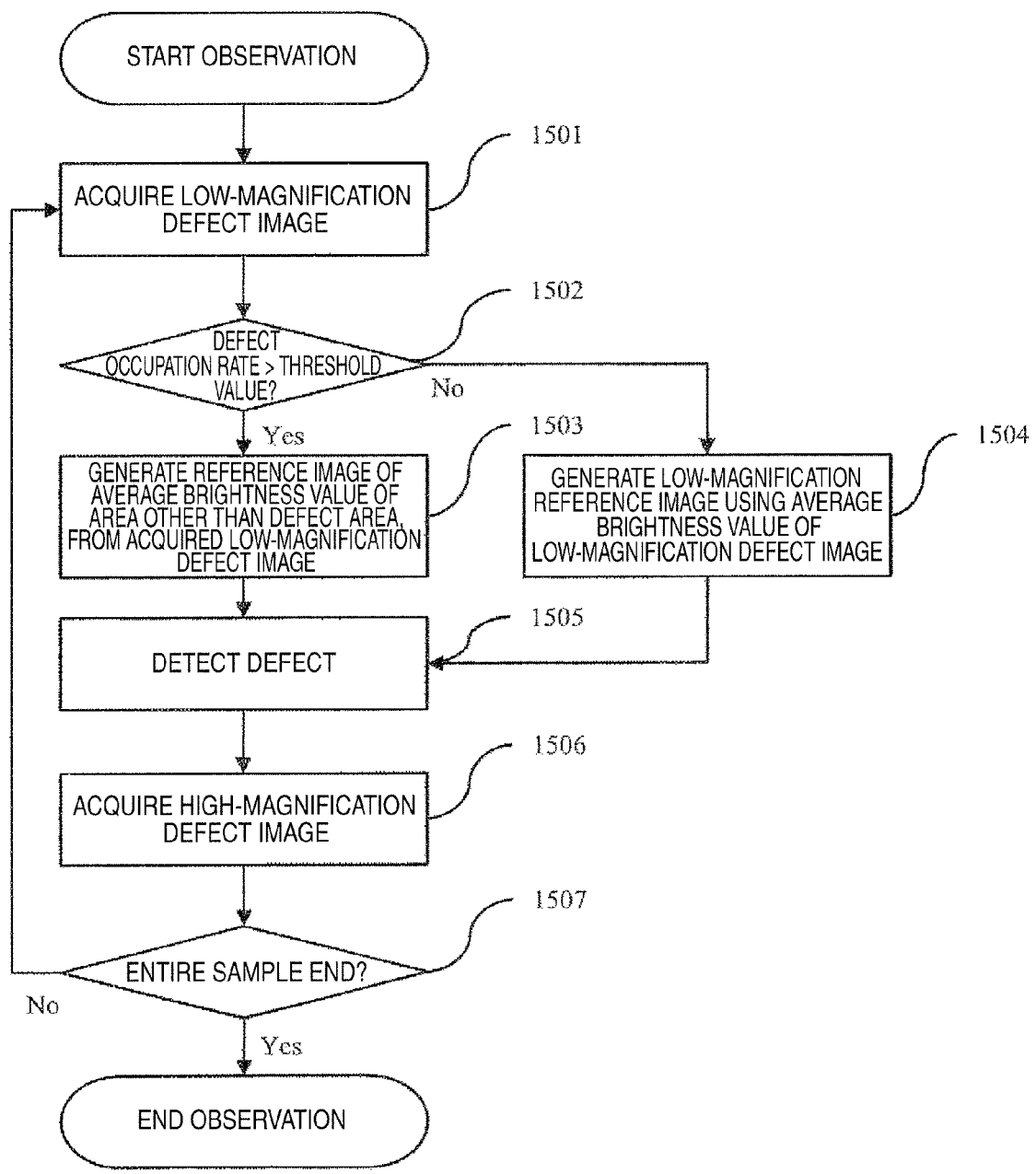
FIG. 15 is an example of an ADR flowchart according to Embodiment 5.

FIG. 15 is an example of a flowchart of ADR illustrating a method, different from Embodiment 4, to avoid the case in which a representative low-magnification reference image is not an ideal reference image, which rarely occurs. First, a low-magnification defect image is acquired (1501) and a defect occupation rate of a defect area in the acquired low-magnification defect image is calculated and the magnitude with a predetermined threshold value is determined (1502). On the basis of a determination result, it is determined whether a low-magnification reference image is generated using an average brightness value of the low-magnification defect image. Specifically, when a defect occupation rate is low, it is determined that a method of generating the low-magnification reference image using the average brightness value of the low-magnification defect image is effective and the low-magnification reference image is generated from the average brightness value of the low-magnification defect image (1504). Meanwhile, when the defect occupation rate is high, an average brightness value of an area other than a defect area is calculated from an image including an acquired defect to imaging of the low-magnification defect image and a low-magnification reference image is generated using the average brightness value (1503). At this time, the defect area included in the image including the acquired defect is already calculated by ADR or ADC processing using the defect image as an inspected target.

Next, the low-magnification reference image generated by 1503 or the low-magnification reference image generated by 1504 and the low-magnification defect image acquired by 1501 are compared and a difference is detected as a defect area (1505). Finally, an enlarged image of the detected defect area is acquired as a high-magnification defect image (1506). Processing of 1501 to 1506 is executed on entire inspection target samples (1507).

In FIG. 15, because the low-magnification reference image is generated using the average brightness value from the area other than the defect area in the acquired defect image (1503) after the defect occupation rate determination processing (1502), a newest low-magnification defect image acquired in the ADR sequence can be used. Thereby, stable defect detection according to a change in visibility by a material quality or a structure at an observation point can be expected.

In addition, if a low-magnification reference image is generated every time, an operation cost increases. For this reason, before the ADR sequence starts, the defect area may be excluded from the acquired defect image in advance and the low-magnification reference image may be generated using the average brightness. The generated low-magnification reference image may be registered in a recipe in which an execution condition of the ADR is described, for example. In this way, the low-magnification reference image generated by considering the reference image acquired in the past can be used without deteriorating the throughput of the ADR. Therefore, stable defect detection can be realized.

When the low-magnification reference image is generated by 1503, an extraction result of the defect area by the ADR or the ADC remains on the acquired defect image. For this reason, the average brightness value of the area other than the defect area can be calculated while an operation cost is suppressed. When the extraction result of the defect area does not remain, the low-magnification defect image and the low-magnification reference image may be compared again and the defect area may be extracted. However, because the operation cost increases, an optimal method may be selected by comparing the methods described to FIG. 14 and considering a balance of the acquired defect detection precision and the operation cost.

Figure 16:
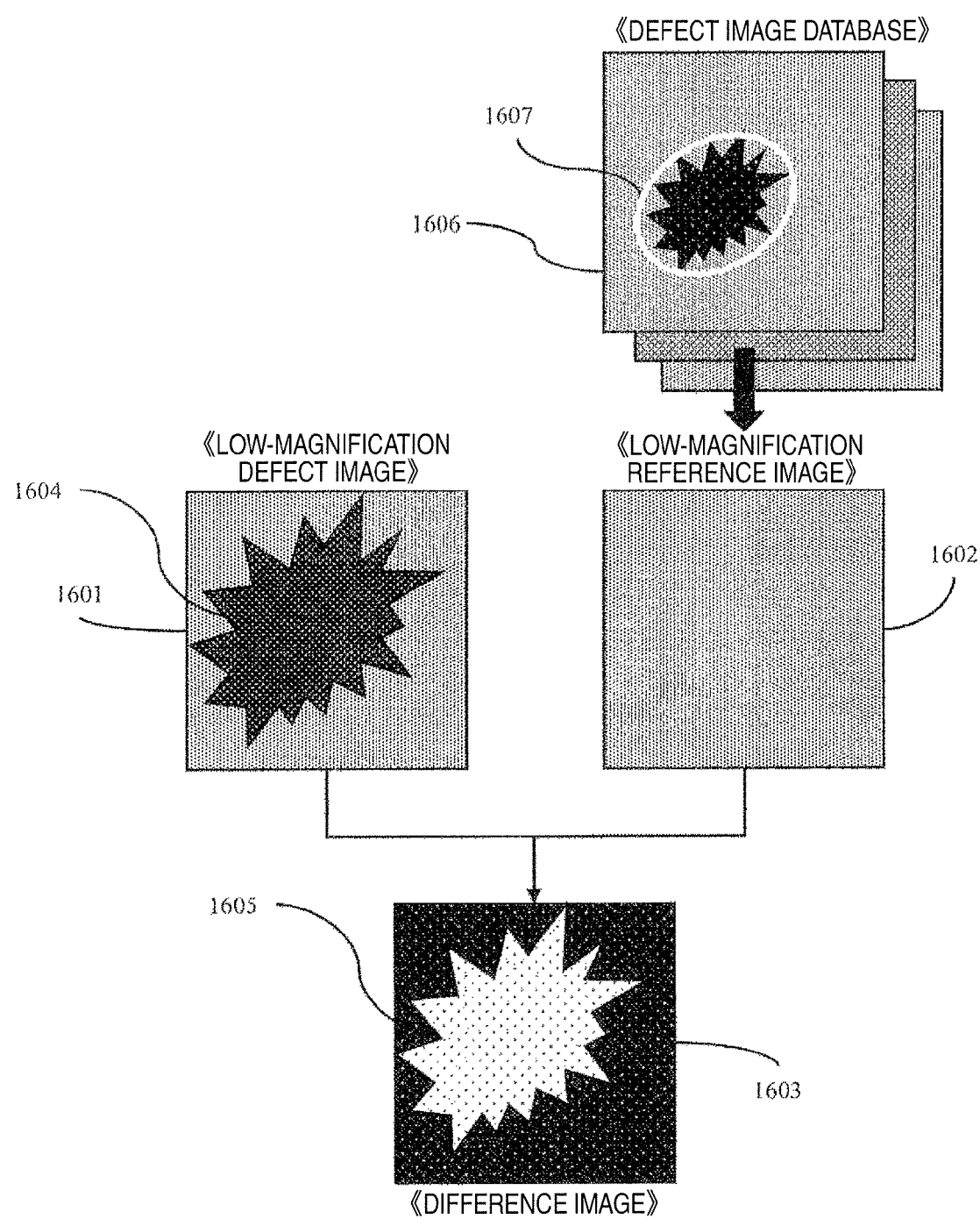
FIG. 16 is an example of a schematic diagram illustrating a defect detection method according to Embodiment 5.

FIG. 16 is an example of a schematic diagram illustrating the defect detection method described in FIG. 15. First, an average brightness of an area other than a defect area 1607 is calculated from one or more acquired defect images 1606 and a low-magnification reference image 1602 is generated using an average brightness value. When a defect occupation rate of an acquired low-magnification defect image 1601 is calculated and the defect occupation rate is high, the low-magnification defect image 1601 and the low-magnification reference image 1602 are compared in a unit of a pixel. Meanwhile, when it is determined that the defect area is small and the defect occupation rate is low, using the same method as the method described in FIG. 6 or 7, the image generated from the average brightness value of the low-magnification defect image is used as the low-magnification reference image and the low-magnification reference image and the low-magnification defect image are compared. When a difference of gradation values is equal to or more than a threshold value by comparison, it is determined that a significant difference exists. In the difference image 1603, pixels in which it is determined that the significant difference exists are shown by white and pixels in which it is determined that the significant difference does not exist are shown by black.

As such, the defect occupation rate is calculated by the defect occupation rate determination processing unit 305 using the low-magnification defect image 301 as an input. When the defect occupation rate is high, the reference image generation processing unit 306 generates the low-magnification reference image 307 using the average brightness value of the area other than the defect area in the acquired low-magnification defect image 303 and when the defect occupation rate is low, the reference image generation processing unit 306 generates the low-magnification reference image 307 from the average brightness value of the low-magnification defect image. The defect detection processing unit 308 compares the low-magnification defect image 301 and the low-magnification reference image 307 output from the reference image generation processing unit 306 and outputs a difference thereof as the defect coordinates 309.

According to this method, when the defect occupation rate is low, the low-magnification reference image generated using the average brightness value of the low-magnification defect image is used for the defect detection, so that stable defect detection can be realized for the change in the brightness due to the noises or the material quality or structure at the observation coordinates. When the defect occupation rate of the low-magnification defect image is high, the average brightness value of the area other than the defect area is calculated from one or more acquired defect images and the low-magnification reference image is generated using the average brightness value. Therefore, stable generation of the low-magnification reference image is enabled for the change in the brightness due to the noises or the material quality or structure at the observation coordinates. The case in which the representative low-magnification reference image is not the ideal reference image, which rarely occurs, can be avoided.

Embodiment 6

In this embodiment, a method of calculating a defect occupation rate will be described. The method of calculating the defect occupation rate according to this embodiment can be applied to any method of Embodiments 1 to 5. Because the configurations described in FIGS. 1 to 3 and the content described in FIGS. 4 to 16 are the same as those in this embodiment, explanation thereof is omitted.

Figure 17:
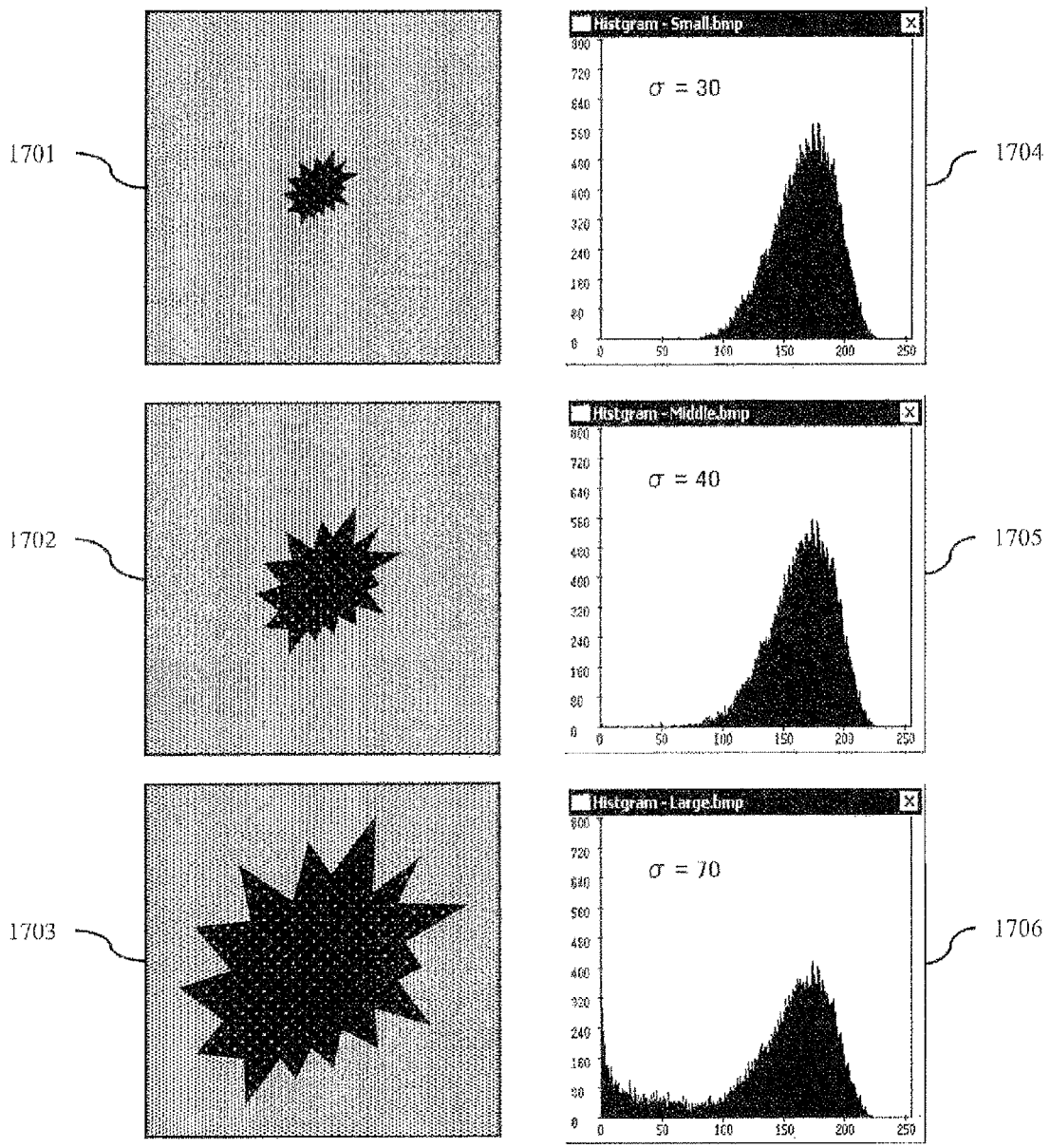
FIG. 17 is an example of a schematic diagram illustrating a method of calculating a defect occupation rate described in Embodiment 6.

FIG. 17 is an example of a schematic diagram illustrating a method of calculating a defect occupation rate in a defect image. FIG. 17 illustrates an example of the case of calculating the defect occupation rate, on the basis of a brightness distribution of pixels included in the defect image.

An example of the case in which a defect area is small is shown in a defect image 1701, an example of the case in which a defect area is middle is shown in a defect image 1702, and an example of the case in which a defect area is large is shown in a defect image 1703. At a right side of the image, a histogram of a brightness distribution calculated for each image and a standard deviation σ of the brightness distribution are displayed. The standard deviation of the brightness distribution corresponding to the defect image 1701 in which the defect area is small is σ=30 (1704). The standard deviation of the brightness distribution corresponding to the defect image 1702 in which the defect area is middle is σ=40 (1705) and has a large value as compared with 1704 in which the defect area is small. In addition, the standard deviation of the brightness distribution corresponding to the defect image 1703 in which the defect area is large is σ=70 (1706) and has a large value as compared with 1704 in which the defect area is small and 1705 in which the defect area is middle. As such, because the standard deviation of the brightness distribution and the defect occupation rate are in a monotonous correlation, it can be determined that the defect occupation rate is large, when the standard deviation of the brightness distribution is more than a certain threshold value.

The calculation of the defect occupation rate can be executed by the entire control unit and analysis unit 113 of FIG. 1, the operation/analysis unit 201 of FIG. 2, and the defect occupation rate determination processing unit 305 of FIG. 3. Of course, the calculation may be executed by other processing unit.

As such, the defect occupation rate of the defect image can be calculated simply by using the standard deviation of the brightness distribution of the defect image.

Here, the method of calculating the defect occupation rate using the standard deviation of the brightness distribution of the defect image has been described. However, parameters other than the standard deviation may be used. In addition, the method of calculating the defect occupation rate is not limited to the above method.

Embodiment 7

In this embodiment, a method of calculating a defect occupation rate, which is different from the method according to Embodiment 6, will be described. The method of calculating the defect occupation rate according to this embodiment can be applied to any method of Embodiments 1 to 5. Because the configurations described in FIGS. 1 to 3 and the content described in FIGS. 4 to 16 are the same as those in this embodiment, explanation thereof is omitted.

Figure 18:
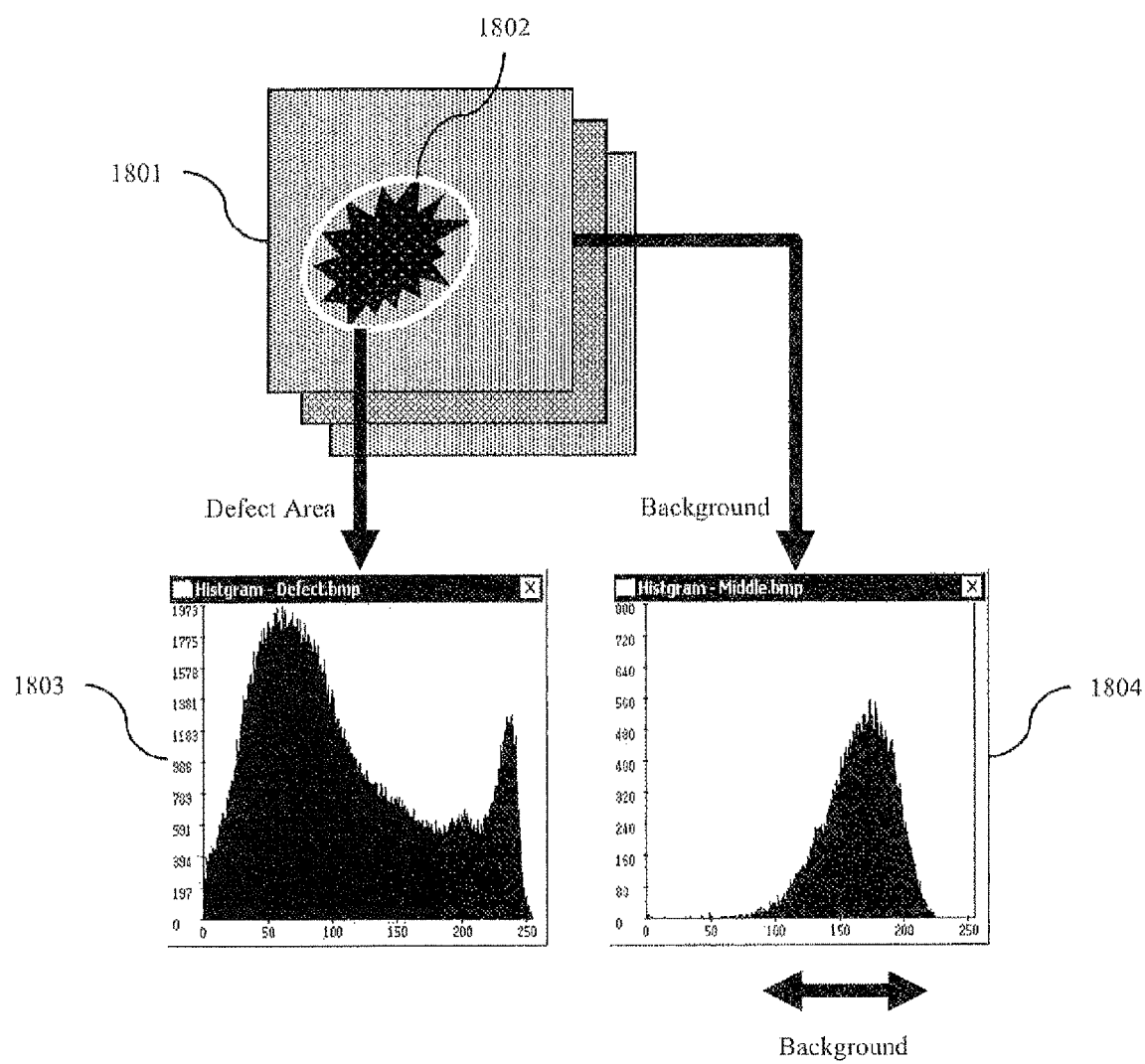
FIG. 18 is an example of a schematic diagram illustrating a method of calculating a defect occupation rate described in Embodiment 7.

FIG. 18 is an example of a schematic diagram illustrating a method of calculating a defect occupation rate from a brightness distribution of a defect area/background of a defect image. First, an image 1801 including one or more defects acquired before acquisition of an inspected image is separated into a defect area 1802 and a background portion other than the defect area and a brightness distribution is calculated. If a result obtained by ADR or ADC with respect to the image 1801 including the defect is used, a defect area can be easily calculated while an operation cost is suppressed.

In an example of FIG. 18, because a brightness of the defect area is low (dark), a state in which the brightness is distributed greatly in the region having the low brightness can be confirmed in a brightness portion 1803 of the defect area. Meanwhile, in a brightness distribution 1804 of the background portion other than the defect area, the distribution is concentrated in a range of brightness values from 100 to 220. From a result, the number of pixels in which the brightness value is beyond the range of 100 to 220 is counted as defect candidates and can be converted into a defect occupation rate. The range of the brightness values used for calculation of the defect occupation rate may be set by a recipe by an operator and may be automatically updated when the defect area is calculated.

As such, the range of the brightness values to be determined as the defect candidates is calculated previously from the brightness distribution of the image including the defect acquired in the past, the pixels corresponding to the range in the defect image to calculate the defect occupation rate are counted as the defect area, and the defect occupation rate can be calculated easily.

If the method according to this embodiment is compared with the method of calculating the defect occupation rate according to Embodiment 6, it is necessary to set the range of the brightness values counted as the defect candidates in advance. However, if the result calculated by the ADR or the ADC is used, the range setting is easily automated and thus, the workload of the operator is small. Because range setting optimal to the focused defect kind is enabled, detailed setting is enabled. By executing the detailed setting, a defect kind to be ignored, called a nuisance defect, can be excluded. For example, as illustrated in FIG. 18, when a defect kind to be recognized as the defect takes a characteristic brightness distribution, a brightness range corresponding to the brightness distribution is counted as the defect area. Meanwhile, when the defect kind to be ignored without being recognized as the defect, such as the nuisance defect, takes a characteristic brightness distribution, the brightness range corresponding to the brightness distribution is not counted as the defect area, so that a defect occupation rate can be calculated for only desired defect kinds.

Embodiment 8

In this embodiment, a method of determining a threshold value when a standard deviation of a brightness distribution of a defect image is used as a threshold value of a defect occupation rate determination processing will be described. The method of determining the threshold value according to this embodiment can be applied to any method of Embodiments 1 to 5. Because the configurations described in FIGS. 1 to 3 and the content described in FIGS. 4 to 18 are the same as those in this embodiment, explanation thereof is omitted.

Figure 19:
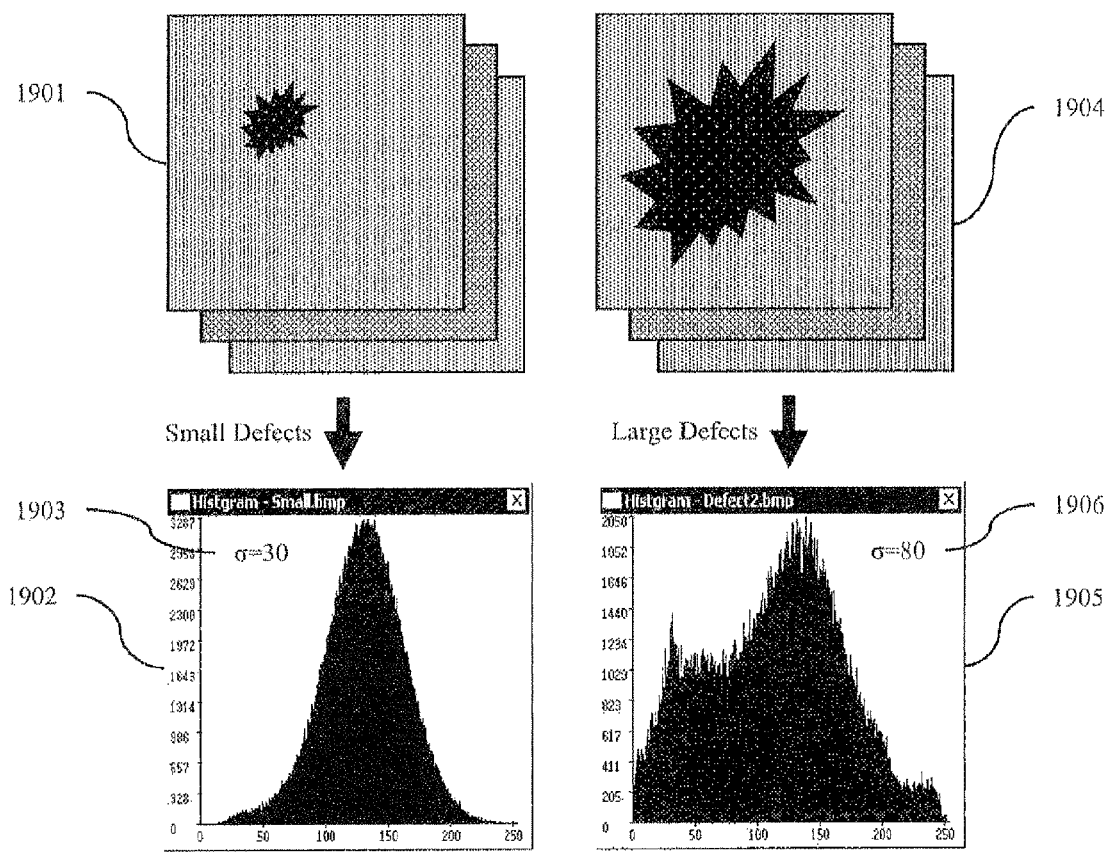
FIG. 19 is an example of a schematic diagram illustrating a method of determining a defect occupation rate described in Embodiment 8.

FIG. 19 is an example of a schematic diagram of a method using a standard deviation of a brightness distribution of a defect image as a threshold value of defect occupation rate determination processing. First, a plurality of images are classified into a plurality of groups according to magnitudes of defects. Specifically, the plurality of images are classified into a group to be determined as an enormous defect and a group other than the group. An image in which it is determined that a defect occupation rate is low is selected in 1901 and an image in which it is determined that the defect occupation rate is high is selected in 1904. The image can be selected by an operator through a GUI displayed on a display. However, candidates of defect images are automatically selected in advance on the basis of a defect detection result of ADR or ADC, so that the workload of the operator can be reduced.

In FIG. 19, an average brightness distribution and a standard deviation are calculated for each group, with respect to defect image sets of each group classified on the basis of the defect occupation rate. A variation of a brightness distribution 1902 of a defect image set 1901 in which it is determined that the defect occupation rate is low is small and a standard deviation 1903 becomes σ=30. Meanwhile, a variation of a brightness distribution 1905 of a defect image set 1904 in which it is determined that the defect occupation rate is low is relatively large and a standard deviation becomes σ=80.

The calculation of the standard deviation of the brightness distribution of the defect image can be realized by the entire control unit and analysis unit 113 of FIG. 1, the operation/analysis unit 201 of FIG. 2, and the defect occupation rate determination processing unit 305 of FIG. 3. Of course, the standard may be executed by other processing unit.

The standard deviation showing the variation of the brightness distribution of the defect image selected as described above is displayed, so that the operator can easily determine a determination threshold value of the defect occupation rate.

If an image in which a defect having a size equal to or more than a specific size is detected is automatically selected on the basis of a defect detection result of ADR or ADC and a standard deviation of a brightness distribution of a selected defect image set is calculated, the determination threshold value of the defect occupation rate can be automatically set or automatically updated.

Even in which the operator manually selects the defect image, instead of the automatic selection, if the defect image of the selection candidate is previously selected as a default in ADR or ADC on a selection screen, efficiency of selection work of the operator can be improved.

Embodiment 9

In this embodiment, a method of selecting the plurality of defect detection methods described in Embodiments 1 to 8 will be described. Because the configurations described in FIGS. 1 to 3 and the content described in FIGS. 4 to 19 are the same as those in this embodiment, explanation thereof is omitted.

Figure 20:
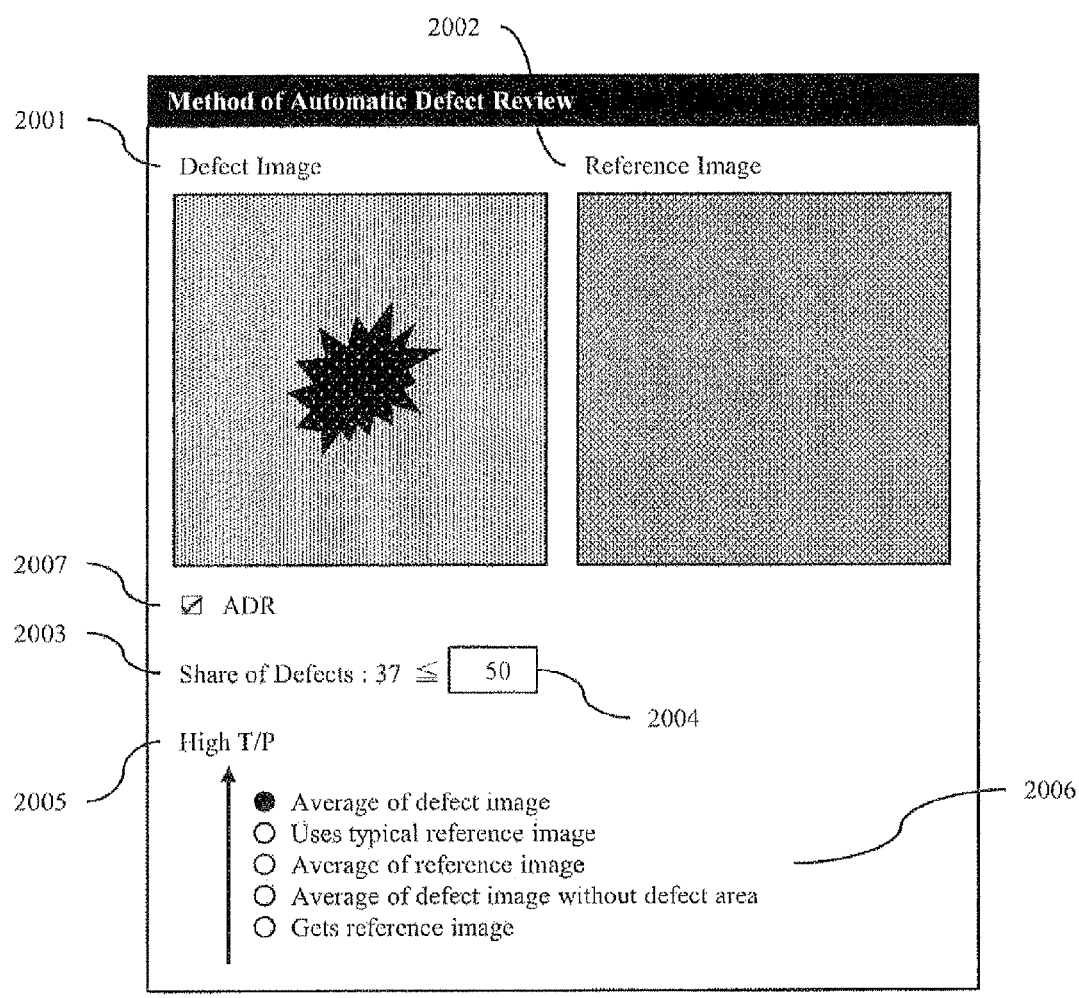
FIG. 20 is an example of a GUI capable of selecting a defect detection method described in Embodiment 9.

FIG. 20 is an example of a GUI that can select a defect detection method. A sample of a low-magnification defect image is displayed in 2001 and a defect occupation rate in the low-magnification defect image is displayed in 2003. The method according to Embodiment 6 or 7 can be applied to the calculation of the defect occupation rate. However, the present invention is not limited thereto. When a plurality of images can be selected, the plurality of images and a defect occupation rate of each image or an average value of defect occupancies of each image may be displayed.

A value of 2004 becomes a determination threshold value of the defect occupation rate. The determination threshold value of the defect occupation rate can be input by an operator. However, the determination threshold value can be automatically set by the method described in Embodiment 8. Even in the case in which the operator inputs and sets the determination threshold value, if a value automatically set as an initial value is displayed, the value can become one of determination standards when the operator sets the threshold value. In an example of FIG. 20, because the defect occupation rate of the low-magnification defect image is equal to or smaller than the threshold value, it is determined that the defect occupation rate of the low-magnification defect image is low and defect detection processing of a rear step is executed.

The plurality of methods of generating or acquiring the reference image, described in the embodiments, are written together in 2006 and the operator can select the method. As displayed in 2005, if each defect detection method is arranged in order of the high processing speeds, each defect detection method becomes one of determination standards when the operator selects the defect detection method. In 2002, a low-magnification reference image is displayed to correspond to the defect detection method selected in 2006.

When an ADR check box 2007 is set to ON, it is effective to display a result obtained by detecting the defect by the selected defect detection method.

As such, the low-magnification defect image of the observation target, the defect occupation rate thereof, the threshold value of the defect occupation rate, the low-magnification reference image corresponding to the selected defect detection method, and the defect detection method are displayed, so that propriety of the selected defect detection method can be easily confirmed. The GUI can be mounted on the entire control unit and analysis unit 113 of FIG. 1 and the operation/analysis unit 201 of FIG. 2. Of course, the GUI may be mounted to other processing unit.

The present invention is not limited to the embodiments described above and various modifications are included. For example, the embodiments are described in detail to facilitate the description of the present invention and are not limited to embodiments in which all of the described configurations are included. In addition, a part of the configurations of the certain embodiment can be replaced by the configurations of another embodiment or the configurations of another embodiment can be added to the configurations of the certain embodiment. In addition, for a part of the configurations of the individual embodiments, other configurations can be added, removed, or replaced.

In addition, a part or all of the individual configurations, functions, processing units, and processing mechanisms may be designed by integrated circuits and may be realized by hardware. In addition, the individual configurations and functions may be realized by software by analyzing programs for realizing the functions by a processor and executing the programs by the processor. Information such as the programs, the tables, and the files for realizing the individual functions may be stored in a recording device such as a memory, a hard disk, and a solid state drive (SSD) or a recording medium such as an IC card, an SD card, and an optical disk.

In addition, only control lines or information lines necessary for explanation are illustrated and the control lines or information lines do not mean all control lines or information lines necessary for a product. In actuality, almost all configurations may be connected to each other.

REFERENCE SIGNS LIST

101: electron gun
102: lens
103: scanning deflector
104: objective lens
105: sample
106: stage
107: primary electron beam
108: secondary particle
109: secondary particle detector
110: electronic optical system control unit
111: A/D conversion unit
112: stage control unit
113: entire control/analysis unit
114: image processing unit
115: operation unit
116: storage device
117: optical microscope
118: SEM-type defect observation device
119: LAN
120: recipe management device
121: defect information database
201: operation/analysis unit
202: defect data storage unit
203: image data storage unit
204: analysis parameter storage unit
205: analysis result storage unit
301: low-magnification defect image
302: low-magnification reference image
303: enormous defect determination processing unit
304: reference image generation processing unit
305: low-magnification reference image
306: defect detection processing unit
307: defect coordinates
501: defect image
502: reference image
503: difference image
504: defect
505: detected defect area
701: defect image
702: reference image generated using average brightness value of defect image
703: difference image
704: defect
705: detected defect area
801: defect image
802: reference image generated using average brightness value of defect image
803: difference image
804: enormous defect
805: detected defect area
1001: defect image
1002: reference image
1003: difference image
1004: defect
1005: detected defect area
1201: defect image
1202: reference image generated using average brightness value of representative reference image
1203: difference image
1204: defect
1205: detected defect area
1206: representative reference image
1401: defect image
1402: reference image generated using average brightness value of acquired reference image
1403: difference image
1404: defect
1405: detected defect area
1406: acquired reference image
1601: defect image
1602: reference image generated using average brightness value of area other than defect from acquired defect image
1603: difference image
1604: defect
1605: detected defect area
1606: acquired defect image
1607: defect area
1701: image having low defect occupation rate
1702: image having middle defect occupation rate
1703: image having high defect occupation rate
1704: brightness distribution histogram of image having low defect occupation rate and standard deviation
1705: brightness distribution histogram of image having middle defect occupation rate and standard deviation
1706: brightness distribution histogram of image having high defect occupation rate and standard deviation
1801: defect image
1802: defect area
1803: brightness distribution of defect area
1804: brightness distribution of background portion other than defect area
1901: defect image set
1902: brightness distribution
1903: standard deviation
1904: defect image group
1905: brightness distribution
1906: standard deviation
2001: defect image
2002: reference image corresponding to selected defect detection method
2003: defect occupation rate
2004: defect occupation rate determination threshold value 2005: defect detection method arranged in order of throughput
2006: selectable defect detection method
2007: ADR execution check box

The invention claimed is:

1. A defect observation device that compares an inspected image and a reference image and detects a defect area included in the inspected image, the defect observation device comprising:
a defect occupation rate determination processing unit that calculates a defect occupation rate to be a ratio of the defect area in the inspected image to an area of the inspected image, determines the magnitude of the defect occupation rate, and determines a single threshold value,
wherein it is determined, based on whether the defect occupation rate is higher or lower than the single threshold value, whether an image, which is configured by pixels having an average brightness value of a plurality of pixels included in the inspected image, is generated as the reference image,
wherein, when the defect occupation rate is higher than the single threshold value, the image acquisition unit newly images an area assumed as an area where a defect does not exist as the reference image, and
when the defect occupation rate is lower than the single threshold value, the reference image generation processing unit generates the image configured by the pixels having the average brightness value of the plurality of pixels included in the inspected image as the reference image.

2. The defect observation device according to claim 1,
wherein, when the defect occupation rate is higher than the single threshold value, the reference image generation processing unit generates an image configured by pixels having an average brightness value of an image acquired before acquisition of the inspected image and not including a defect as the reference image, and
when the defect occupation rate is lower than the single threshold value, the reference image generation processing unit generates the image configured by the pixels having the average brightness value of the plurality of pixels included in the inspected image as the reference image.

3. The defect observation device according to claim 2,
wherein the reference image generation processing unit generates the reference image using an image not including a plurality of defects.

4. The defect observation device according to claim 1,
wherein, when the defect occupation rate is higher than the single threshold value, the reference image generation processing unit generates an image configured by pixels having an average brightness value of an area other than a defect area from an image acquired before acquisition of the inspected image and including a defect as the reference image, and
when the defect occupation rate is lower than the single threshold value, the reference image generation processing unit generates the image configured by the pixels having the average brightness value of the plurality of pixels included in the inspected image as the reference image.

5. The defect observation device according to claim 1,
wherein the defect occupation rate determination processing unit calculates the defect occupation rate on the basis of a brightness distribution of the pixels included in the inspected image.

6. The defect observation device according to claim 1, further comprising:
an operation unit that calculates a range of brightness values to be determined as defects, on the basis of a brightness distribution of a defect area in an image acquired before acquisition of the inspected image and including the defects, and
wherein the defect occupation rate determination processing unit calculates the defect occupation rate from the number of pixels configuring the inspected image and included in the range of the brightness values.

7. The defect observation device according to claim 1,
wherein the defect occupation rate determination processing unit uses the single threshold value on the basis of an average brightness distribution of a plurality of images included in each of a plurality of groups classified by magnitudes of defects.

8. The defect observation device according to claim 1, further comprising:
a display unit that displays a screen to enable selection of a plurality of methods to generate or acquire the reference image.

9. A defect observation method that compares an inspected image and a reference image and detects a defect area included in the inspected image, the defect observation device comprising:
calculating a defect occupation rate to be a ratio of the defect area in the inspected image to an area of the inspected image and determining the magnitude of the defect occupation rate and a single threshold value; and
determining, based on whether the defect occupation rate is higher or lower than the single threshold value, whether an image, which is configured by pixels having an average brightness value of brightness values of a plurality of pixels included in the inspected image, is generated as the reference image;
wherein, when the defect occupation rate is higher than the single threshold value, an area assumed as an area where a defect does not exist as the reference image is newly imaged as the reference image, and
when the defect occupation rate is lower than the single threshold value, the image configured by the pixels having the average brightness value of the brightness values of the plurality of pixels included in the inspected image is generated as the reference image.

10. The defect observation method according to claim 9,
wherein, when the defect occupation rate is higher than the single threshold value, an image configured by pixels having an average brightness value of an image acquired before acquisition of the inspected image and not including a defect is generated as the reference image, and
when the defect occupation rate is lower than the single threshold value, the image configured by the pixels having the average brightness value of the plurality of pixels included in the inspected image is generated as the reference image.

11. The defect observation method according to claim 10,
wherein the reference image is generated using an image not including a plurality of defects.

12. The defect observation method according to claim 9,
wherein, when the defect occupation rate is higher than the single threshold value, an image configured by pixels having an average brightness value of an area other than a defect area in an image acquired before acquisition of the inspected image and including a defect is generated as the reference image, and when the defect occupation rate is lower than the single threshold value, the image configured by the pixels having the average brightness value of the inspected image is generated as the reference image.

13. A defect observation device that compares an inspected image and a reference image and detects a defect area included in the inspected image, the defect observation device comprising:
  an image processor which generates an image based on a detection signal acquired by scanning a charged particle beam on a sample; and
  a control computer which is connected to the image processor,
  wherein the defect observation device is configured to calculate a defect occupation rate which is a ratio of the defect area in the inspected image acquired based on the detection signal to an area of the inspected image, to generate a reference image based on the inspected image when the defect occupation rate is lower than a single threshold value, to generate a reference image based on an image other than the inspected image when the defect occupation rate is higher than the single threshold value, and to detect a defect in the inspected image by comparing the inspected image with the reference image generated based on the inspected image or the reference image based on the image other than the inspected image;
  wherein, when the defect occupation rate is higher than the single threshold value, an area assumed as an area where a defect does not exist as the reference image is newly imaged as the reference image, and
when the defect occupation rate is lower than the single threshold value, the image configured by the pixels having the average brightness value of the brightness values of the plurality of pixels included in the inspected image is generated as the reference image.

* * * * *